(12) United States Patent
Bednarek et al.

(10) Patent No.: US 10,960,181 B2
(45) Date of Patent: *Mar. 30, 2021

(54) FIXED DIMENSIONAL AND BI-DIRECTIONAL STEERABLE CATHETER CONTROL HANDLE

(71) Applicant: St. Jude Medical, Atrial Fibrillation Division, Inc., St. Paul, MN (US)

(72) Inventors: Michael C. Bednarek, Buffalo, MN (US); Eric J. Wilkowske, North Oaks, MN (US); Richard E. Stehr, Tucson, AZ (US); William E. Butler, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 203 days.

This patent is subject to a terminal disclaimer.

(21) Appl. No.: 16/046,376

(22) Filed: Jul. 26, 2018

(65) Prior Publication Data

US 2019/0015633 A1 Jan. 17, 2019

Related U.S. Application Data

(60) Continuation of application No. 14/851,843, filed on Sep. 11, 2015, now Pat. No. 10,035,000, which is a
(Continued)

(51) Int. Cl.
*A61M 25/01* (2006.01)
*A61B 5/042* (2006.01)

(52) U.S. Cl.
CPC ......... *A61M 25/0147* (2013.01); *A61B 5/042* (2013.01); *A61B 5/0422* (2013.01); *A61M 25/0136* (2013.01)

(58) Field of Classification Search
CPC .......... A61M 25/0136; A61M 25/0147; A61M 25/0105; A61M 25/0158
(Continued)

(56) References Cited

U.S. PATENT DOCUMENTS 3,375,583 A 4/1968 Blank et al.
4,203,430 A 5/1980 Takahashi
(Continued)

FOREIGN PATENT DOCUMENTS

EP 1205208 A1 5/2002
GB 1170018 A 12/1969
(Continued)

*Primary Examiner* — Scott J Medway
(74) *Attorney, Agent, or Firm* — Dykema Gossett PLLC

(57) ABSTRACT

An apparatus for imparting a tensile force to deflect a distal portion of a catheter while maintaining its exterior dimensions may include a handle grip including a cross-section of generally predetermined exterior dimensions, and a longitudinal axis. A flexible elongate member may include proximal and distal end portions, with the proximal end portion being coupled to the handle grip. An adjustment knob may include a cross-section of generally predetermined exterior dimensions, and is rotatably coupled to the handle grip around the longitudinal axis. An elongate deflection member may be operably coupled to the adjustment knob and to the distal end portion of the elongate member. Rotation of the adjustment knob may impart a tensile force to the deflection member thereby causing the distal end portion of the elongate member to deflect from a prior configuration while maintaining the generally predetermined exterior dimensions of the handle grip and the adjustment knob.

20 Claims, 22 Drawing Sheets

Related U.S. Application Data division of application No. 13/692,597, filed on Dec. 3, 2012, now Pat. No. 9,132,258, which is a continuation of application No. 12/346,653, filed on Dec. 30, 2008, now Pat. No. 8,323,239, which is a continuation of application No. 11/023,667, filed on Dec. 28, 2004, now Pat. No. 7,691,095.

(58) Field of Classification Search
USPC ............... 604/523, 528, 95.01, 264; 600/585
See application file for complete search history.

(56) References Cited

U.S. PATENT DOCUMENTS

| | | |
|---|---|---|
| 4,483,326 A | 11/1984 | Yamaka et al. |
| 4,586,923 A | 5/1986 | Gould et al. |
| 4,757,827 A | 7/1988 | Buchbinder et al. |
| 4,886,067 A | 12/1989 | Palermo |
| 4,960,134 A | 10/1990 | Webster, Jr. |
| 5,125,895 A | 6/1992 | Buchbinder et al. |
| 5,125,896 A | 6/1992 | Hojeibane |
| 5,163,911 A | 11/1992 | Sirimanne et al. |
| 5,167,221 A | 12/1992 | Chikama |
| 5,269,757 A | 12/1993 | Fagan et al. |
| RE34,502 E | 1/1994 | Webster, Jr. |
| 5,277,199 A | 1/1994 | DuBois et al. |
| 5,281,217 A | 1/1994 | Edwards et al. |
| 5,304,351 A | 4/1994 | Tanaka et al. |
| 5,318,525 A | 6/1994 | West et al. |
| 5,327,889 A | 7/1994 | Imran |
| 5,327,905 A | 7/1994 | Avitall |
| 5,327,906 A | 7/1994 | Fideler et al. |
| 5,330,466 A | 7/1994 | Imran |
| 5,342,295 A | 8/1994 | Imran |
| 5,354,297 A | 10/1994 | Avitall |
| 5,359,994 A | 11/1994 | Krauter et al. |
| 5,364,351 A | 11/1994 | Heinzelman et al. |
| 5,364,352 A | 11/1994 | Cimino et al. |
| 5,372,587 A | 12/1994 | Hammerslang et al. |
| 5,383,923 A | 1/1995 | Webster, Jr. |
| 5,389,073 A | 2/1995 | Imran |
| 5,391,147 A | 2/1995 | Imran et al. |
| 5,395,327 A | 3/1995 | Lundquist et al. |
| 5,395,328 A | 3/1995 | Ockuly et al. |
| 5,395,329 A | 3/1995 | Fleischhacker et al. |
| 5,397,304 A | 3/1995 | Truckai |
| 5,431,168 A | 7/1995 | Webster, Jr. |
| 5,445,148 A | 8/1995 | Jaraczewski et al. |
| 5,462,527 A | 10/1995 | Oldham et al. |
| 5,478,330 A | 12/1995 | Imran et al. |
| 5,487,385 A | 1/1996 | Avitall |
| 5,487,757 A | 1/1996 | Truckai et al. |
| 5,527,279 A | 6/1996 | Imran |
| 5,533,967 A | 7/1996 | Imran |
| 5,545,200 A | 8/1996 | West et al. |
| 5,549,542 A | 8/1996 | Kovalcheck |
| 5,562,619 A | 10/1996 | Mirarchi et al. |
| 5,582,609 A | 12/1996 | Swanson et al. |
| 5,588,964 A | 12/1996 | Imran et al. |
| 5,611,777 A | 3/1997 | Bowden et al. |
| 5,626,136 A | 5/1997 | Webster, Jr. |
| 5,656,029 A | 8/1997 | Imran et al. |
| 5,656,030 A | 8/1997 | Hunjan et al. |
| 5,662,606 A | 9/1997 | Cimino et al. |
| 5,755,760 A | 5/1998 | Maguire et al. |
| 5,779,669 A | 7/1998 | Haissaguerre et al. |
| 5,807,249 A | 9/1998 | Qin et al. |
| 5,826,576 A | 10/1998 | West |
| 5,827,272 A | 10/1998 | Breining et al. |
| 5,827,278 A | 10/1998 | Webster |
| 5,836,947 A | 11/1998 | Fleischman et al. |
| 5,842,984 A | 12/1998 | Avitall |
| 5,843,031 A | 12/1998 | Hermann et al. |
| 5,843,076 A | 12/1998 | Webster, Jr. et al. |
| 5,857,997 A | 1/1999 | Cimino et al. |
| 5,861,024 A | 1/1999 | Rashidi |
| 5,865,800 A | 2/1999 | Mirarchi et al. |
| 5,885,278 A | 3/1999 | Fleischman et al. |
| 5,897,529 A | 4/1999 | Ponzi |
| 5,910,129 A | 6/1999 | Haissaguerre et al. |
| 5,916,213 A | 6/1999 | Haissaguerre et al. |
| 5,916,214 A | 6/1999 | Cosio et al. |
| 5,921,924 A | 7/1999 | Avitall |
| 5,931,811 A | 8/1999 | Haissaguerre et al. |
| 5,935,102 A | 8/1999 | Bowden et al. |
| 5,938,616 A | 8/1999 | Eaton et al. |
| 5,944,690 A | 8/1999 | Falwell et al. |
| 5,957,943 A | 9/1999 | Vaitekunas |
| 5,987,344 A | 11/1999 | West |
| 5,993,462 A | 11/1999 | Pomeranz et al. |
| 6,002,955 A | 12/1999 | Willems et al. |
| 6,024,722 A | 2/2000 | Rau et al. |
| 6,027,473 A | 2/2000 | Ponzi |
| 6,033,403 A | 3/2000 | Tu et al. |
| 6,048,329 A | 4/2000 | Thompson et al. |
| 6,059,739 A | 5/2000 | Baumann |
| 6,064,902 A | 5/2000 | Haissaguerre et al. |
| 6,066,125 A | 5/2000 | Webster, Jr. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,083,222 A | 7/2000 | Klein et al. |
| 6,090,104 A | 7/2000 | Webster, Jr. |
| 6,123,699 A | 9/2000 | Webster, Jr. |
| 6,138,043 A | 10/2000 | Avitall |
| 6,149,663 A | 11/2000 | Strandberg et al. |
| 6,156,034 A | 12/2000 | Cusio et al. |
| 6,165,188 A | 12/2000 | Saadat et al. |
| 6,169,916 B1 | 1/2001 | West |
| 6,171,277 B1 | 1/2001 | Ponzi |
| 6,178,354 B1 | 1/2001 | Gibson |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,200,315 B1 | 3/2001 | Gaiser et al. |
| 6,203,507 B1 | 3/2001 | Wadsworth et al. |
| 6,203,525 B1 | 3/2001 | Whayne et al. |
| 6,210,362 B1 | 4/2001 | Ponzi |
| 6,210,407 B1 | 4/2001 | Webster |
| 6,214,002 B1 | 4/2001 | Fleischman et al. |
| 6,221,087 B1 | 4/2001 | Anderson et al. |
| 6,224,587 B1 | 5/2001 | Gibson |
| 6,241,754 B1 | 6/2001 | Swanson et al. |
| 6,308,091 B1 | 10/2001 | Avitall |
| 6,375,654 B1 | 4/2002 | McIntyre |
| 6,394,976 B1 | 5/2002 | Winston et al. |
| 6,430,426 B2 | 8/2002 | Avitall |
| 6,454,758 B1 | 9/2002 | Thompson et al. |
| 6,464,645 B1 | 10/2002 | Park et al. |
| 6,468,260 B1 | 10/2002 | Bumbalough et al. |
| 6,485,455 B1 | 11/2002 | Thompson et al. |
| 6,500,167 B1 | 12/2002 | Webster |
| 6,544,215 B1 | 4/2003 | Bencini et al. |
| 6,554,794 B1 | 4/2003 | Mueller et al. |
| 6,582,536 B2 | 6/2003 | Shimada |
| 6,602,242 B1 | 8/2003 | Fung et al. |
| 6,652,506 B2 | 11/2003 | Bowe et al. |
| 6,829,497 B2 | 12/2004 | Mogul |
| 6,913,594 B2 | 7/2005 | Coleman et al. |
| 6,991,616 B2 | 1/2006 | Bencini et al. |
| 7,056,314 B1 | 6/2006 | Florio et al. |
| 7,263,397 B2 | 8/2007 | Hauck et al. |
| 7,269,453 B2 | 9/2007 | Mogul |
| 7,374,553 B2 | 5/2008 | Koerner et al. |
| 7,386,339 B2 | 6/2008 | Strommer et al. |
| 7,416,547 B2 | 8/2008 | Hill et al. |
| 7,615,044 B2 | 11/2009 | Scheibe et al. |
| 7,691,095 B2 | 4/2010 | Bednarek et al. |
| 7,727,228 B2 | 6/2010 | Abboud et al. |
| 7,780,593 B2 | 8/2010 | Ueno et al. |
| 7,803,130 B2 | 9/2010 | Ryan et al. |
| 7,881,809 B2 | 2/2011 | Rashidi |
| 8,323,239 B2 | 12/2012 | Bednarek et al. |

(56) References Cited

U.S. PATENT DOCUMENTS

| | | |
|---|---|---|
| 8,460,237 B2 | 6/2013 | Schultz |
| 8,858,495 B2 | 10/2014 | Tegg et al. |
| 9,132,258 B2 | 9/2015 | Bednarek et al. |
| 2002/0095146 A1 | 7/2002 | Hutchins et al. |
| 2007/0260223 A1 | 11/2007 | Scheibe et al. |
| 2007/0299424 A1 | 12/2007 | Cumming et al. |
| 2008/0009745 A1 | 1/2008 | Hossack et al. |
| 2008/0119727 A1 | 5/2008 | Barbagli et al. |
| 2009/0105640 A1 | 4/2009 | Bednarek et al. |
| 2010/0069921 A1 | 3/2010 | Miller et al. |
| 2010/0168735 A1 | 7/2010 | Deno et al. |
| 2010/0217235 A1 | 8/2010 | Thorstenson et al. |
| 2015/0105655 A1 | 4/2015 | Tegg et al. |

FOREIGN PATENT DOCUMENTS

| | | |
|---|---|---|
| WO | 97/33526 A2 | 9/1997 |
| WO | 98/33429 A2 | 8/1998 |

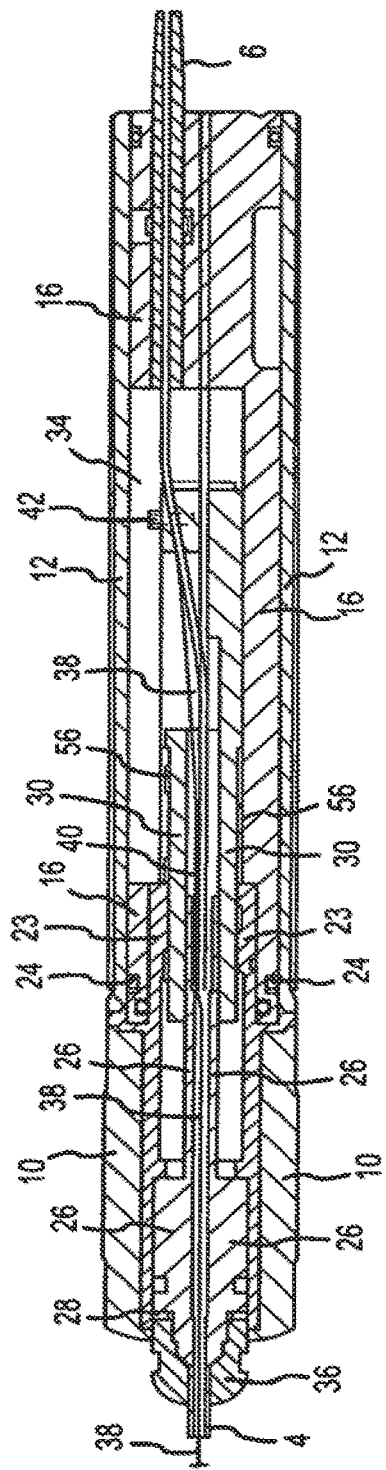
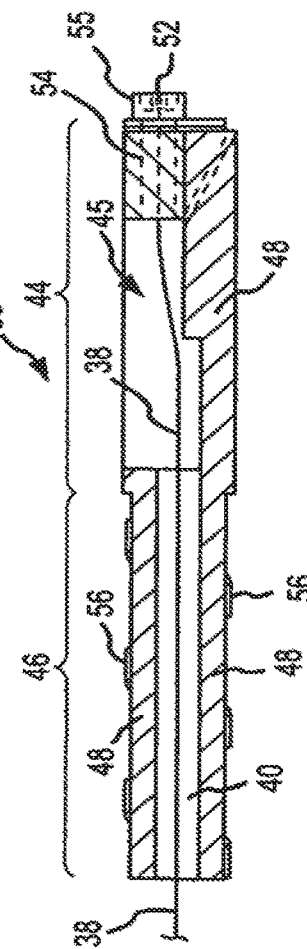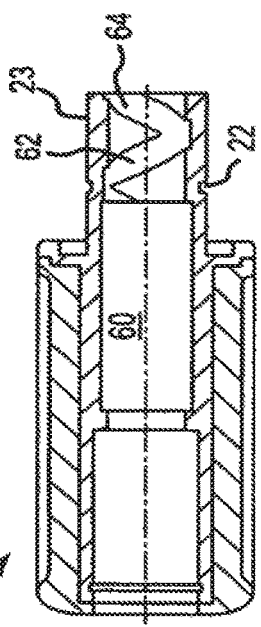

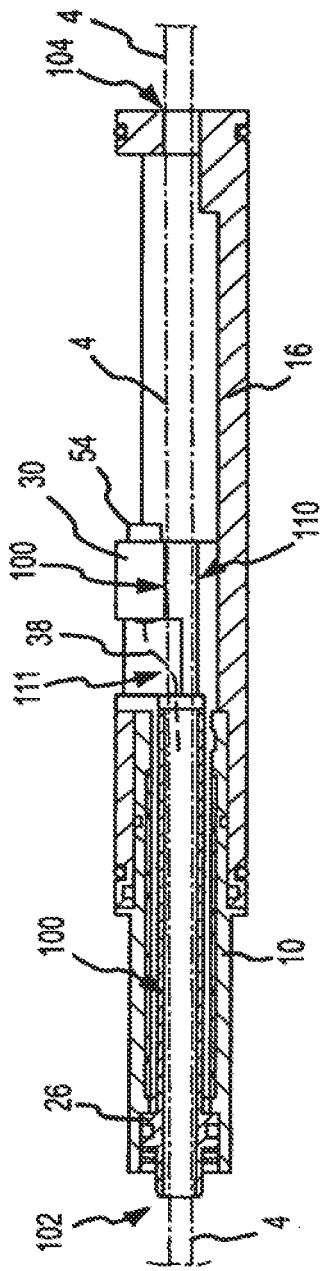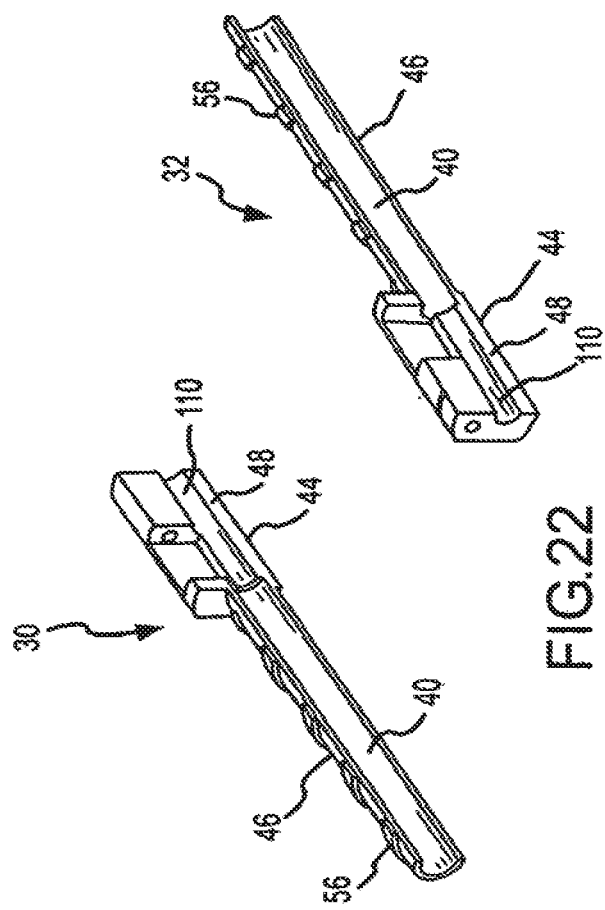

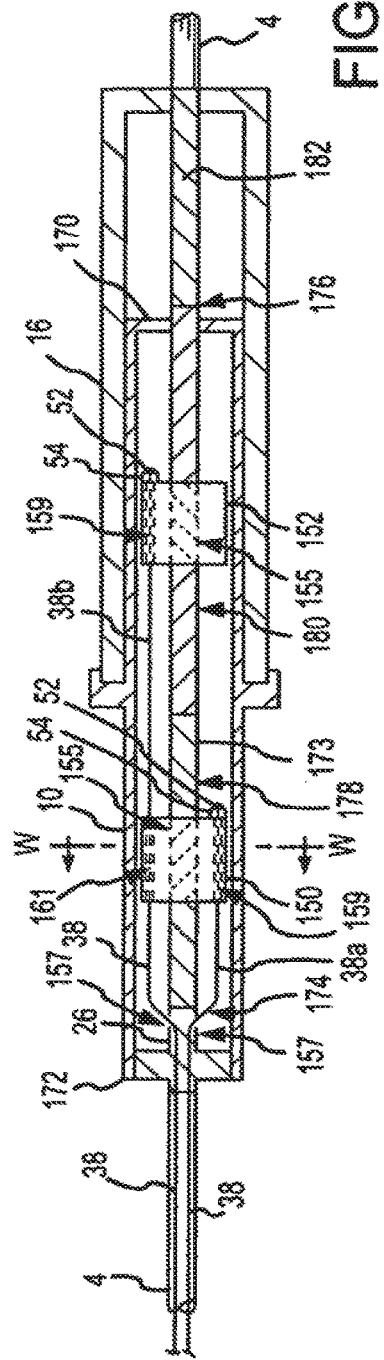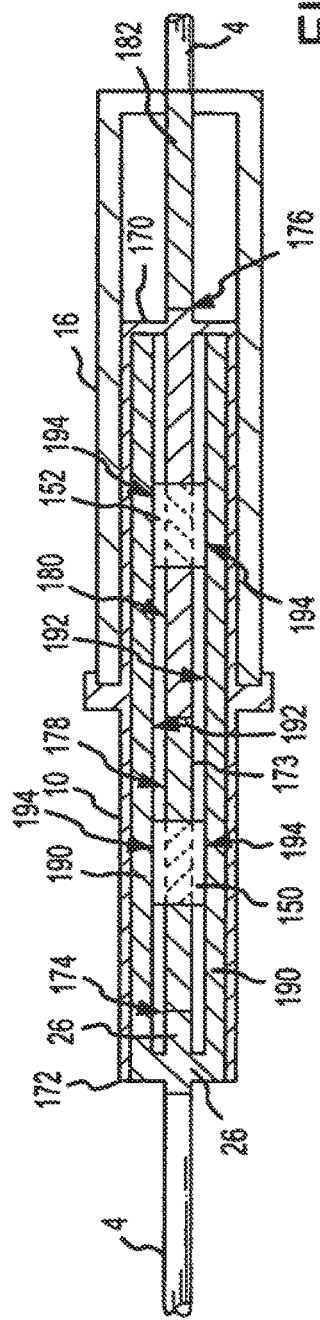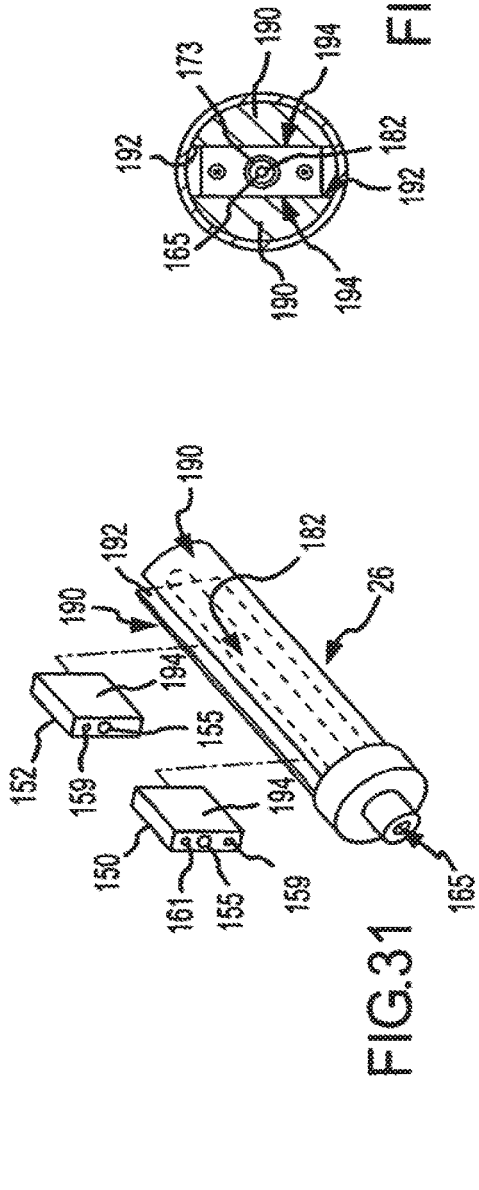

FIXED DIMENSIONAL AND BI-DIRECTIONAL STEERABLE CATHETER CONTROL HANDLE

CROSS-REFERENCE TO RELATED APPLICATIONS

This application is a continuation of U.S. application Ser. No. 14/851,843 filed 11 Sep. 2015 (the '843 application), which is a divisional of U.S. application Ser. No. 13/692,597 filed 3 Dec. 2012, now U.S. Pat. No. 9,132,258 (the '597 application), which is a continuation of U.S. application Ser. No. 12/346,653 filed 30 Dec. 2008, now U.S. Pat. No. 8,323,239 (the '653 application), which is a continuation of U.S. application Ser. No. 11/023,667 filed 28 Dec. 2004, now U.S. Pat. No. 7,691,095 (the '667 application). The '843 application, the '597 application, the '653 application, and the '667 application are hereby incorporated by reference as though fully set forth herein.

BACKGROUND OF THE INVENTION a. Field of the Invention

The present invention relates to catheters and sheaths and methods of using catheters and sheaths. More particularly, the present invention relates to a fixed dimensional control handle for steerable catheters and sheaths and methods of manufacturing and using such an handle, with the control handle generally maintaining its exterior dimensions during operation thereof.

b. Background Art

Catheters (i.e. catheters or sheaths) that have flexible tubular bodies with deflectable distal ends and control handles for controlling distal end deflection are used for many noninvasive medical procedures. For example, catheters having conductive electrodes along the distal ends of their bodies are commonly used for intra-cardiac electrophysiology studies. The distal end of a catheter body is typically placed into a patient's heart to monitor and/or record the intra-cardiac electrical signals during electrophysiology studies or during intra-cardiac mapping. The orientation or configuration of the distal end is controlled via an actuator located on the catheter's control handle, which remains outside the patient's body. The electrodes conduct cardiac electrical signals to appropriate monitoring and recording devices that are operatively connected at the control handle.

Typically, a catheter body is cylindrical and electrically non-conductive. The catheter body includes a flexible tube constructed from polyurethane, nylon or other electrically non-conductive flexible material. The catheter body further includes braided steel wires or other non-metallic fibers in its wall as reinforcing elements. Each electrode has a relatively fine electrically conductive wire attached thereto and extending through the catheter body. The conductive wire extends from the distal end to a proximal end where electrical connectors such as plugs or jacks are provided to be plugged into a corresponding socket provided in a recording or monitoring device.

The distal portion of the catheter body is selectively deformed into a variety of curved configurations using the actuator on the control handle. The actuator is commonly internally linked to the distal portion of the catheter body by at least one deflection wire. Some catheter bodies employ a single deflection wire, which is pulled (i.e., placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

To deform the distal end of the catheter body into a variety of configurations, a more recent catheter design employs a pair of deflection wires that are adapted such that one of the deflection wires carries a compressive force when the other deflection wire carries a tensile force. In such catheters, where the deflection wires are adapted to carry both compressive and tension loads, the deflection wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

Prior art control handles for controlling distal end deflection of catheter bodies have several drawbacks that adversely impact the handles' ability to be operated precisely by a single hand. First, the control handles are often excessively bulky. Second, the control handles are often inadequate with respect to their ability to provide finely controlled deflection adjustment for the distal end of the catheter body. Third, the control handles often provide inadequate mechanical advantage that is less than desirable and, as result, require significant effort to operate on the part of a user. Fifth, once a desired body distal end deflection has been reached, the control handles typically require the physician to take a conscious step to maintain the catheter at the desired deflection. Sixth, the wire displacement mechanisms within the control handles have a tendency to permanently deform the deflection wires. Seventh, the wire displacement mechanisms within the control handles typically make it difficult, if not impossible, to provide a lumen that runs uninterrupted from the proximal end of the control handle to the distal end of the catheter body.

There is a need in the art for a catheter control handle that offers improved single hand operation and deflection adjustment of the distal end of the catheter body. There is also a need in the art for such a handle with a lumen there through. There is also a need in the art for a method of manufacturing and using such a control handle.

BRIEF SUMMARY OF INVENTION

A fixed dimensional and bi-directional steerable catheter control handle may include an apparatus for imparting a tensile force to deflect a distal portion of a catheter while maintaining its exterior dimensions. The apparatus may include a handle grip including generally oval or circular cross-sections of generally predetermined exterior dimensions, and a longitudinal axis. A flexible elongate member may include proximal and distal end portions, with the proximal end portion being coupled to the handle grip. An adjustment knob may include a generally circular cross-section of generally predetermined exterior dimensions, and may be rotatably coupled to the handle grip around the longitudinal axis of the handle grip. One or more elongate deflection members may be operably coupled to the adjustment knob and to the distal end portion of the elongate member. Rotation of the adjustment knob may impart a tensile force to the elongate deflection member thereby causing the distal end portion of the elongate member to deflect from a prior configuration while maintaining the generally predetermined exterior dimensions of the handle grip and the adjustment knob.

For the apparatus described above, in an embodiment, the elongate deflection member may include a filament, a braided cord, or a resin-based member. In an embodiment, the adjustment knob may be operably coupled to an intermediate body portion or a distal portion of the handle grip. In an embodiment, the elongate deflection member may include a first pull wire. The apparatus, in an embodiment, may include one or more additional pull wires operably coupled to the adjustment knob.

For the apparatus described above, in an embodiment, the apparatus may include means for simultaneously imparting a tensile force to the first pull wire and releasing a tensile force on the additional pull wire. The adjustment knob may include an interior surface forming an aperture generally orthogonally oriented with respect to the longitudinal axis of the handle grip, with the interior surface including one or more sets of threaded grooves which cooperate with the means. The means may include a pair of generally axially displaceable members disposed within the handle grip, and rotation of the adjustment knob may impart opposing forces to the axially displaceable members.

For the apparatus described above, in an embodiment, the elongate member may include one or more longitudinal lumens. In an embodiment, the apparatus may include one or more electrodes coupled to the elongate member. The elongate member, in an embodiment, may include a biocompatible electrically insulative material. The electrically insulative material may be a flexible material. Alternatively, the electrically insulative material may include a polyurethane material or a nylon material. The apparatus, in an embodiment, may include one or more reinforcing elements disposed within a portion of the elongate member. The reinforcing element may include braided members, which may include a conductive material.

For the apparatus described above, in an embodiment, the elongate member may include a segment of a braided metallic wire and/or a non-metallic fiber. The apparatus, in an embodiment, may include a hemostasis valve coupled to the handle grip. In an embodiment, an exterior surface of the adjustment knob may includes a generally longitudinal groove and/or a generally longitudinal protuberance.

For the apparatus described above, in an embodiment, the prior configuration may include a substantially straight configuration. In an embodiment, the elongate deflection member may include an elongate wire. In an embodiment, the apparatus may include an anchor ring coupled to the distal portion of the elongate member, and the elongate deflection member may include one or more elongate pull wires coupled to the anchor ring.

In an embodiment, an apparatus for imparting a tensile force to deflect a distal portion of a catheter while maintaining its exterior dimensions may include a handle grip including a cross-section of generally predetermined exterior dimensions, and a longitudinal axis. A flexible elongate member may include proximal and distal end portions, with the proximal end portion being coupled to the handle grip. An adjustment knob may include a cross-section of generally predetermined exterior dimensions, and be rotatably coupled to the handle grip around the longitudinal axis of the handle grip. One or more elongate deflection members may be operably coupled to the adjustment knob and to the distal end portion of the elongate member. Rotation of the adjustment knob may impart a tensile force to the elongate deflection member thereby causing the distal end portion of the elongate member to deflect from a prior configuration while maintaining the generally predetermined exterior dimensions of the handle grip and the adjustment knob.

For the apparatus described above, the handle grip may include a generally oval or circular cross-section, and in an embodiment, the adjustment knob may include a generally circular cross-section.

In an embodiment, an apparatus for imparting a tensile force to deflect a distal portion of a catheter while maintaining its exterior dimensions may include a substantially hollow handle grip having a tactile outer surface having a longitudinal axis. An adjustment knob having a tactile outer surface may be coupled to the handle grip approximately equidistant from the longitudinal axis. A relatively thin elongated flexible body may have a distal end portion and a proximal portion, with the proximal portion coupled to the handle grip. One or more elongated members may be operatively coupled to the adjustment knob and to the distal end portion. Means may be disposed within the handle grip and operatively coupled to the adjustment knob for imparting a tensile force to the elongated member when the adjustment knob is rotated about the longitudinal axis so that the distal end portion of the flexible body deflects from a first configuration to a second configuration. The tactile outer surfaces of the handle grip and the adjustment knob may be substantially unchanged when the flexible body is disposed in the first and second configurations.

For the apparatus described above, the handle grip may include a generally oval or circular cross-section and in an embodiment, the adjustment knob may include a generally circular cross-section.

The foregoing and other aspects, features, details, utilities, and advantages of the invention will be apparent from reading the following description and claims, and from reviewing the accompanying drawings.

BRIEF DESCRIPTION OF THE DRAWINGS

FIG. 3 is a longitudinal sectional elevation of the handle taken along section line AA of FIG. 1.

FIG. 5 is a side elevation of an exemplary slide illustrating a means of securing a deflection wire to the proximal end of the slide.

FIG. 6 is a longitudinal sectional elevation of the adjusting knob taken along section line AA of FIG. 1.

FIG. 21 is a longitudinal sectional elevation taken along section line ZZ in FIG. 20.

FIG. 22 is isometric views of the slides oriented to show their respective portions of the passage and their planar slide faces.

FIG. 29 is a longitudinal sectional elevation of another embodiment of the handle taken along section line YY of FIG. 23.

FIG. 30 is a longitudinal sectional plan view of the handle depicted in FIG. 29 taken along section line VV in FIG. 23 and wherein section line VV forms a plane that is perpendicular to the plane formed by section line YY in FIG. 23.

FIG. 31 is an isometric view of one embodiment of the wire guide.

FIG. 32 is a latitudinal sectional elevation of the handle as taken along section line WW in FIG. 29.

DETAILED DESCRIPTION OF THE INVENTION

Figure 1:
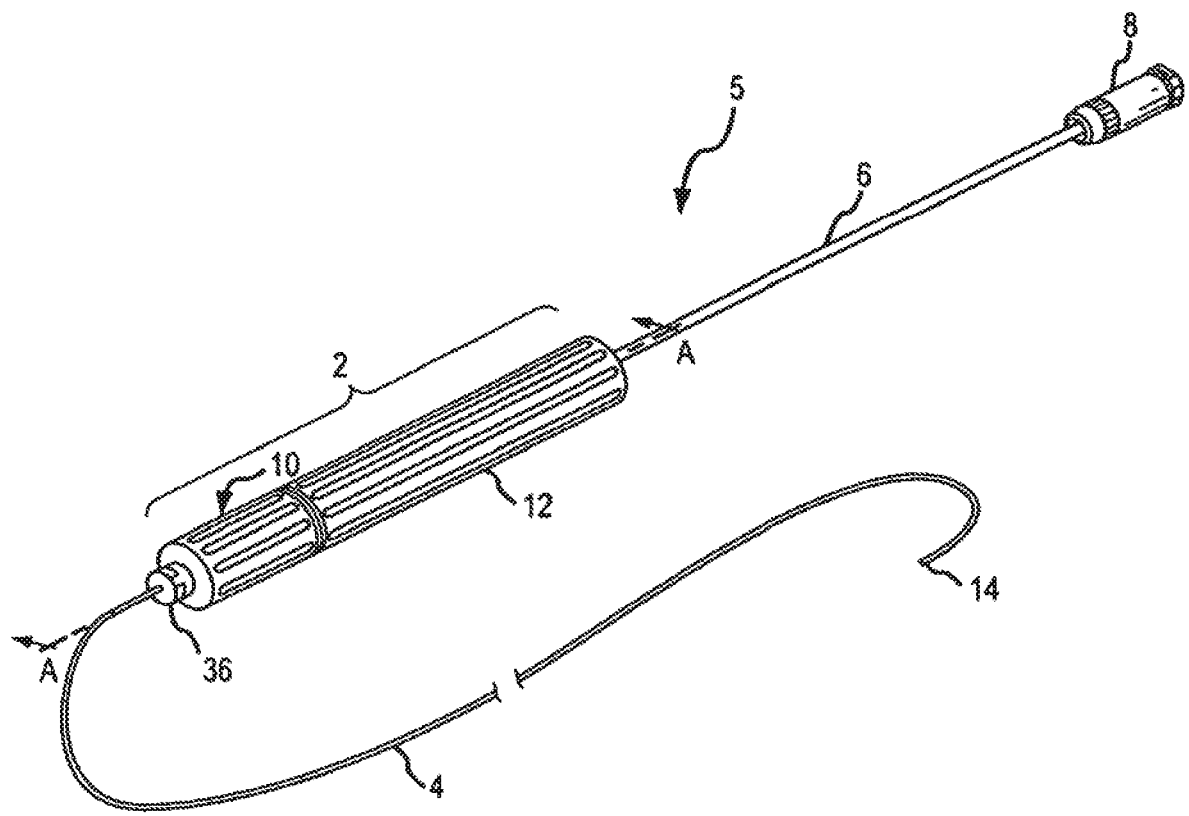
FIG. 1 is an isometric view of one embodiment of the present invention, which is a control handle for a catheter or sheath.

Referring FIG. 1 is an isometric view of one embodiment of the present invention, which is a control handle 2 for a flexible tubular body 4 of a catheter 5. Throughout this specification, the term catheter is meant to include, without limitation, catheters, sheaths and similar medical devices. As shown in FIG. 1, in one embodiment, the distal end of the handle 2 is connected to the catheter body 4 and the proximal end of the handle 2 is connected to tubing 6 that contains electrical wire and extends to an electrical connector 8. The handle 2 includes an adjusting knob 10 and a handle grip 12. As will become clear from this specification, the handle 2 of the present invention is advantageous in that it is compact and allows a user to manipulate the catheter body's extreme distal end 14 in a bi-directional manner by pivoting the adjusting knob 10 relative to the handle grip 12 in one direction or the other about the longitudinal axis of the handle 2. Furthermore, in one embodiment, the handle 2 has a lumen that runs uninterrupted from the proximal end of the handle 2 to the extreme distal end 14 of the catheter body 4. This lumen can be used to provide contrast injection for guide wire insertion.

Figure 2:
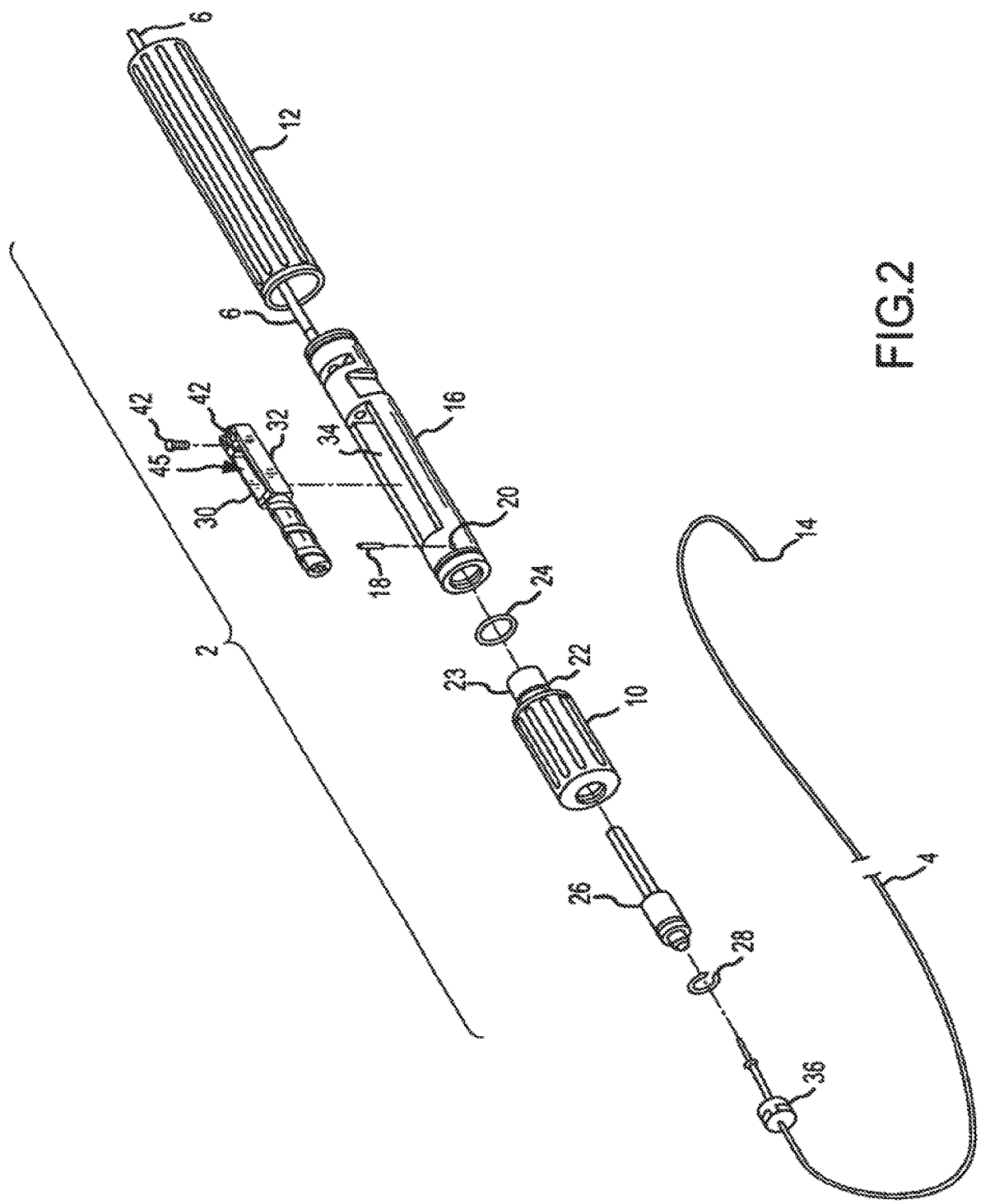
FIG. 2 is an isometric view of the handle exploded to show its various components.

For a more detailed discussion of the handle 2, reference is now made to FIGS. 2 and 3. FIG. 2 is an isometric view of the handle 2 exploded to show its various components. FIG. 3 is a longitudinal sectional elevation of the handle 2 taken along section line AA of FIG. 1.

As shown in FIGS. 2 and 3, the adjusting knob 10 is pivotally attached to a mounting shaft (i.e., a slide base or base portion) 16 contained within the handle grip 12. To pivotally attach the knob 10 to the mounting shaft 16, a dowel pin 18 is inserted into a pinhole 20 in the distal end of the shaft 16 and mates with a groove 22 in a hub portion 23 of the knob 10. A silicone o-ring 24 exists between the hub portion 23 of the knob 10 and the distal end of the shaft 16.

As indicated in FIGS. 2 and 3, a wire guide 26 is positioned within the adjusting knob 10 and is held in place by a retaining ring 28. A right slide or member 30 and a left slide or member 32 are slideably positioned within a slot (i.e., a slide compartment) 34 in the mounting shaft 16. A catheter body-retaining nut 36 is used to secure the catheter body 4 to the distal end of the wire guide 26.

As illustrated in FIG. 3, a pair of deflection wires 38 extend from the extreme distal end 14 of the body 4, through the body 4, the wire guide 26 and a passage 40 formed between the two slides 30, 32, to a point near a proximal portion of the slides 30, 32. Each wire 38 then affixes to an individual slide 30, 32 via a retention screw 42.

Figure 4:
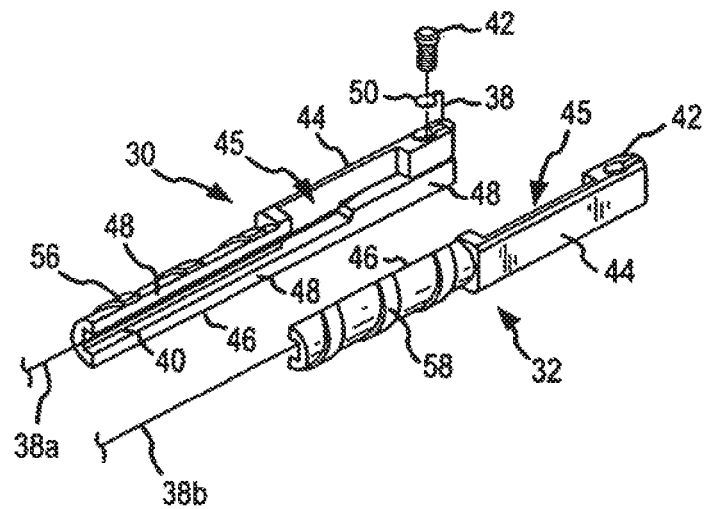
FIG. 4 is an isometric view of the right and left slides with their respective deflection wires attached.

For a more detailed discussion of the slides 30, 32 and their relationship to the deflection wires 38, reference is now made to FIG. 4, which is an isometric view of the deflection wires 38a, 38b attached to the right and left sides 30, 32. As shown in FIG. 4, the slides 30, 32, which are mirror images of each other, each have a rectangular box-like proximal portion 44 and a half-cylinder distal portion 46. Each proximal portion 44 has a generally planar outer sidewall and bottom wall. These planar surfaces slideably displace against the generally planar sides and bottom of the slot 34, which act as thrust surfaces for the slides 30, 32.

Each half-cylinder distal portion 46 is hollowed out along its longitudinal axis to form the passage 40 through which the deflection wires 38a, 38b and, as indicated in FIG. 3, the narrow proximal portion of the wire guide 26 extend when the slides 30, 32 are in the assembled handle 2. Each slide 30, 32 has a planar slide face 48 that is meant to slideably abut against the planar slide face 48 of the opposing slide 30, 32. Thus, as illustrated in FIG. 2, when the planar slide faces 48 of the slides 30, 32 abut against each other and the extreme proximal ends of each slide 30, 32 are flush with each other, the half-cylinder distal portions 46 of each slide 30, 32 combine to form a complete cylinder with a channel or passage 40 there through.

As shown in FIG. 4, in one embodiment, the proximal end of each deflection wire 38a, 38b forms a loop 50 through which retention screw 42 passes to secure the wire 38a, 38b to the proximal portion of the respective slide 30, 32. As indicated in FIG. 5, which is a side elevation of an exemplary slide 30, in one embodiment, the proximal end of each deflection wire 38 forms a knot 52. The wire 38 passes through a hollow tension adjustment screw 54 and the knot 52 abuts against the head 55 of the screw 54, thereby preventing the wire 38 from being pulled back through the screw 54. In one embodiment, the screw's longitudinal axis and the longitudinal axis of the slide 30, 32 are generally parallel. Each tension adjustment screw 54 is threadably received in the proximal end of its respective slide 30, 32. Tension in a wire 38 may be increased by outwardly threading the wire's tension adjustment screw 54. Conversely, tension in a wire 38 may be decreased by inwardly threading the wire's tension adjustment screw 54.

As can be understood from FIG. 4, in one embodiment where the wires 38a, 38b are intended to only transmit tension forces, the wires 38a, 38b may deflect or flex within an open area 45 defined in the proximal portion 44 of each slide 30, 32 when the slides 30, 32 displace distally. Similarly, as can be understood from FIG. 5, in another embodiment where the wires 38 are intended to only transmit tension forces, the wires 38 may slide proximally relative to the screw 54 when the slides 30, 32 displace distally.

As shown in FIG. 4, in one embodiment, the outer circumference of the half-cylinder distal portion 46 of the right slide 30 is threaded with a right-hand thread 56, and the outer circumference of the half-cylinder distal portion 46 of the left slide 32 is threaded with a left-hand thread 58. In one embodiment, the outer circumference of the half-cylinder distal portion 46 of the right slide 30 is threaded with a left-hand thread, and the outer circumference of the half-cylinder distal portion 46 of the left slide 32 is threaded with a right-hand thread.

For a better understanding of the relationship of the slide threads 56, 58 to the rest of the handle 2, reference is now made to FIG. 6, which is a longitudinal sectional elevation of the adjusting knob 10 taken along section line AA of FIG. 1. As indicated in FIG. 6, a cylindrical hole or shaft 60 passes through the knob 10 along the knob's longitudinal axis. In the hub portion 23 of the knob 10, the inner circumferential surface of the shaft 60 has both right hand threads 62 of the knob 10 mate with the right external threads 56 of the right slide 30, and the left internal threads 64 of the knob 10 mate with the left external threads 58 of the left slide 32.

Thus, as can be understood from FIGS. 2, 3, 4 and 6, in one embodiment, as the knob 10 is rotated clockwise relative to the longitudinal axis of the handle 2, the internal and external right threads 62, 56 engage and the internal and external left threads 64, 58 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIGS. 4 and 6, when the knob 10 is rotated such that the right slide 30 is urged distally and the left slide 32 is urged proximally, the deflection wire 38a connected to the right slide 30 is placed into compression and the deflection wire 38b connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38a connected to the right slide 30 is placed into tension and the deflection wire 38b connected to the left slide 32 is placed into compression. This causes the extreme distal end 14 of the catheter body 4 to deflect in a second direction that is opposite the first direction.

The control handle 2 of the present invention as described has several advantages. First, the handle 2 is compact and may be operated with a single hand. Second, the threaded slides 30, 32 and knob 10 allow a physician to make fine, controlled adjustments to the bend in the distal end 14 of the catheter body 4. Third, once the knob 10 is rotated so as to cause a bend in the distal end 14 of the catheter body 4, the threads 56, 58, 62, 64 interact to maintain the bend without requiring any action on the physician's part. Fourth, because the slides 30, 32 simply displace distally and proximally along the longitudinal axis of the handle 2, they are less likely to permanently deform the wires 38 as compared to the wire displacement mechanisms in some prior art handles. Fifth, the threads 56, 58, 62, 64 are mechanically advantageous in that they provide increased deflection wire travel and reduced actuation effort for the physician, as compared to some prior art handles.

Figure 33:
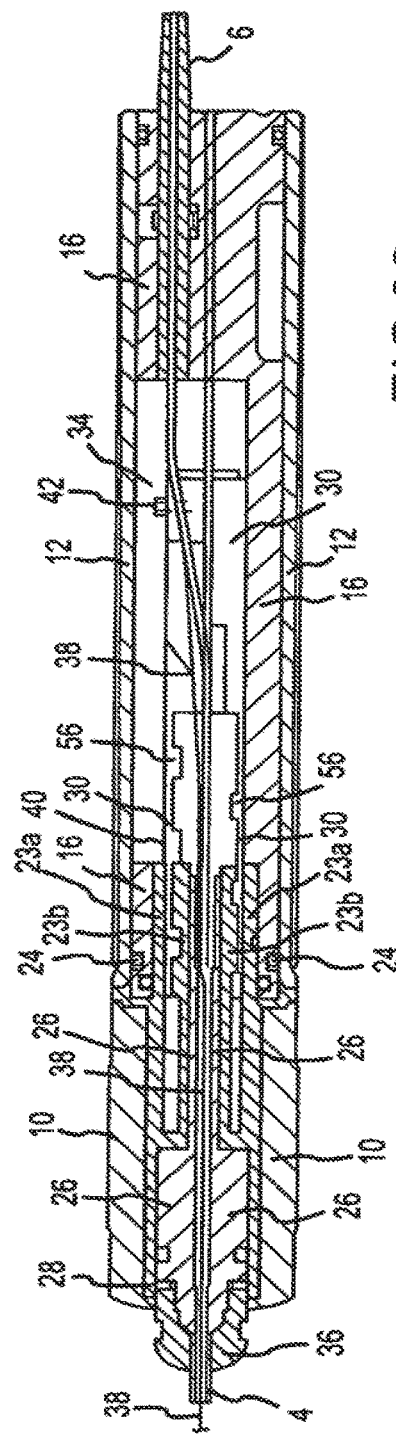
FIG. 33 is a longitudinal sectional elevation of the handle taken along section line AA of FIG. 1.
Figure 34:
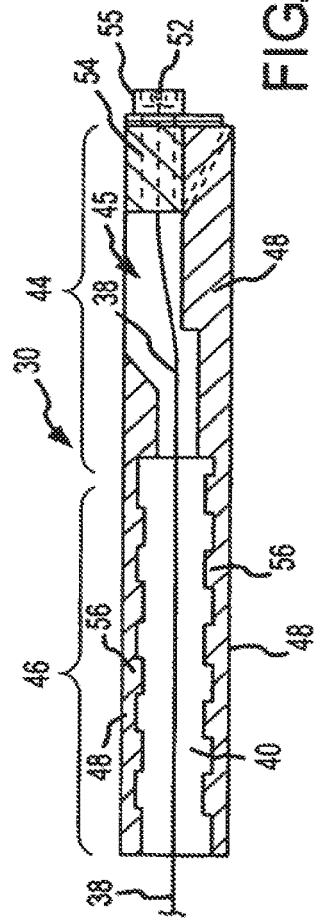
FIG. 34 is a side elevation of an exemplary slide employed in the embodiment depicted in FIG. 33.
Figure 35:
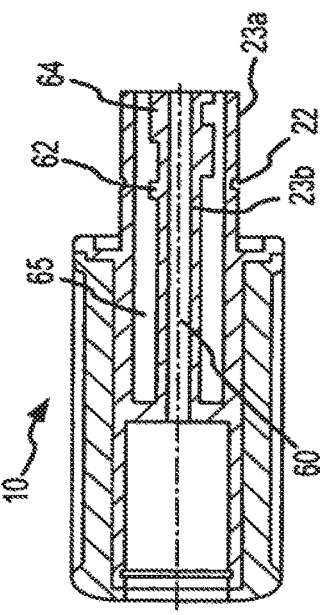
FIG. 35 is a longitudinal sectional elevation of the adjusting knob taken along section line AA of FIG. 1.

While FIGS. 2-6 depict an embodiment where the slides 30, 32 have external threads 56, 58 and the knob 10 has internal threads 62, 64, in other embodiments the threading arrangement is reversed. For a discussion of one such embodiment, reference is made to FIGS. 33-35. FIG. 33 is a longitudinal sectional elevation of the handle 2 taken along section line AA of FIG. 1. FIG. 34 is a side elevation of an exemplary slide employed in the embodiment depicted in FIG. 33. FIG. 35 is a longitudinal sectional elevation of the adjusting knob taken along section line AA of FIG. 1.

A comparison of the embodiment depicted in FIGS. 33-35 to the embodiment depicted in FIGS. 3, 5 and 6 reveals that the two embodiments are generally the same, except as will be described in the following discussion of FIGS. 33-35. Reference numbers utilized in FIGS. 33-35 pertain to the same or similar features identified by the same reference numbers in FIGS. 3, 5 and 6.

As shown in FIG. 33, the adjusting knob 10 is pivotally attached to a mounting shaft (i.e., a slide base or base portion) 16 contained within the handle grip 12. A wire guide 26 is positioned within the adjusting knob 10. Like the embodiment depicted in FIG. 2, the embodiment illustrated in FIG. 33 includes a right slide or member 30 and a left slide or member 32 that are slideably positioned within a slot (i.e., a slide compartment) 34 in the mounting shaft 16.

As can be understood from FIG. 34, the slides 30, 32, which are mirror images of each other, each have a rectangular box-like proximal portion 44 and a distal portion 46 that may be rectangular or half-cylindrical. Each proximal portion 44 has a generally planar outer sidewall and bottom wall. Theses planar surfaces slideably displace against the generally planar sides and bottom of the slot 34, which act as thrust surfaces for the slides 30, 32.

Each distal portion 46 is hollowed out to form half of a cylindrical passage 40 that is created when the slide 30, 32 are abutted against each other in a side-by-side relationship. Thus, each distal portion 46 of each slide 30, 32 includes an inner circumferential surface, which when combined with the inner circumferential surface of the other slide 30, 32, defines the cylindrical passage 40.

As indicated in FIG. 34, in one embodiment, the inner circumferential surface of the right slide 30 is threaded with a right-hand thread 56. Similarly, as can be understood from FIG. 34, the inner circumferential surface of the left slide 32 is threaded with a left-hand thread 58. Thus, the distal portion 46 of each slide 30, 32 is equipped with internal threads. In another embodiment, the inner circumferential surface of the right slide 30 is threaded with a left-hand thread 58. Similarly, the inner circumferential surface of the left slide 32 is threaded with a right-hand thread 56.

Figure 36:
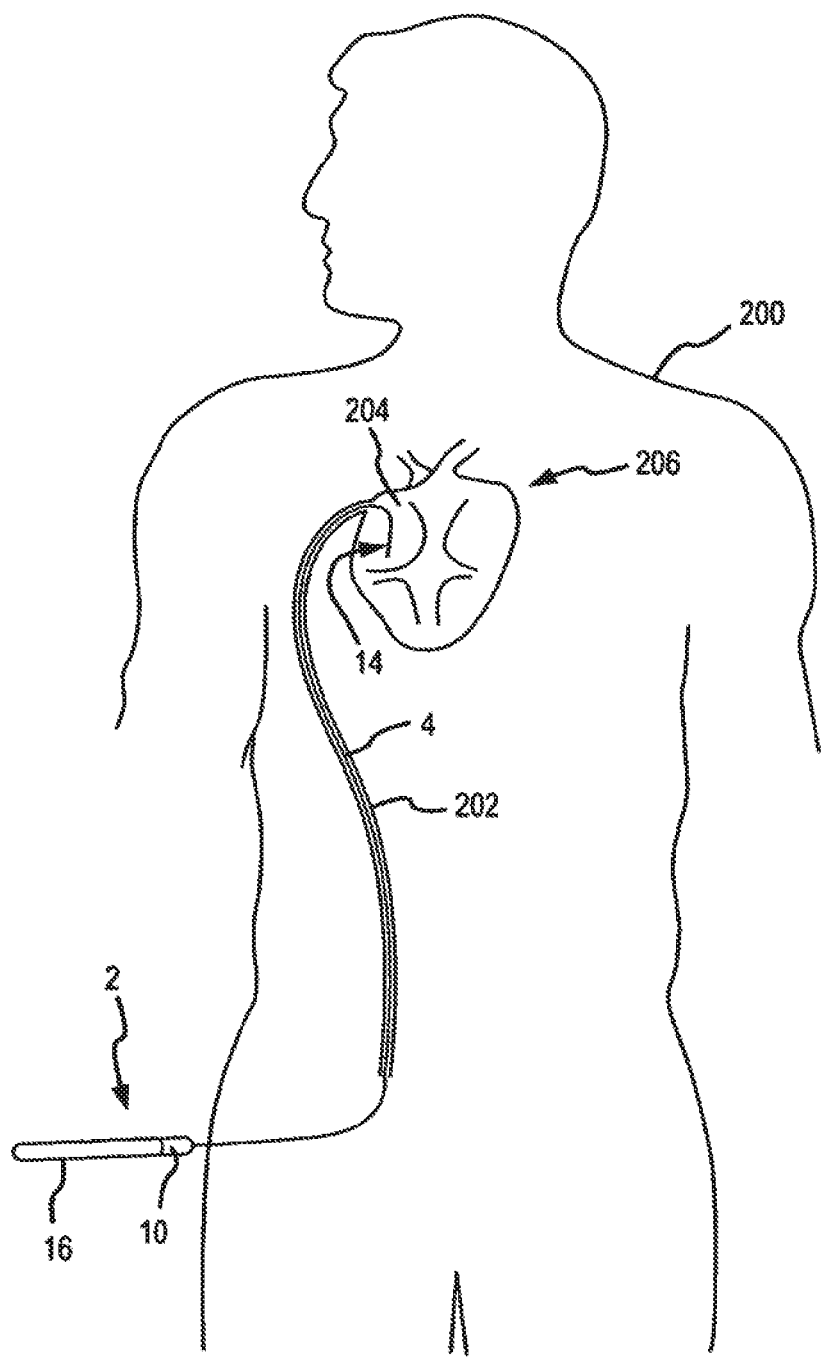
FIG. 36 is a diagrammatic illustration of the control handle of the subject invention being employed in a surgical procedure on a patient.

As indicated in FIG. 36, the knob 10 includes an outer hub 23a surrounding an inner hub 23b. A space 65 exists between, and is defined by, the inner and outer hubs 23a, 23b. The space 65 is adapted to receive the distal ends 46 of each slide 30, 32. The outer circumferential surface of the inner hub 23b has both right hand threads 62 and left hand threads 64. These external threads 62, 64 of the knob 10 mate with the corresponding internal threads 56, 58 of the slides 30, 32. More specifically, the right external threads 62 of the knob 10 mate with the right internal threads 56 of the right slide 30, and the left external threads 64 of the knob 10 mate with the left internal threads 58 of the left slide 32.

As can be understood from FIG. 33, in one embodiment, as the knob 10 is rotated clockwise relative to the longitudinal axis of the handle 2, the internal and external right threads 56, 62 engage and the internal and external left threads 58, 64 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIG. 33, when the knob 10 is rotated such that the right slide 30 is urged distally and the left slide 32 is urged proximally, the deflection wire 38 connected to the right slide 30 is placed into compression and the deflection wire 38 connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38 connected to the right slide 30 is placed into tension and the deflection wire 38 connected to the left slide 32 is placed into compression. This causes the extreme distal end 14 of the catheter body 4 to deflect in a second direction that is opposite the first direction.

Figure 7:
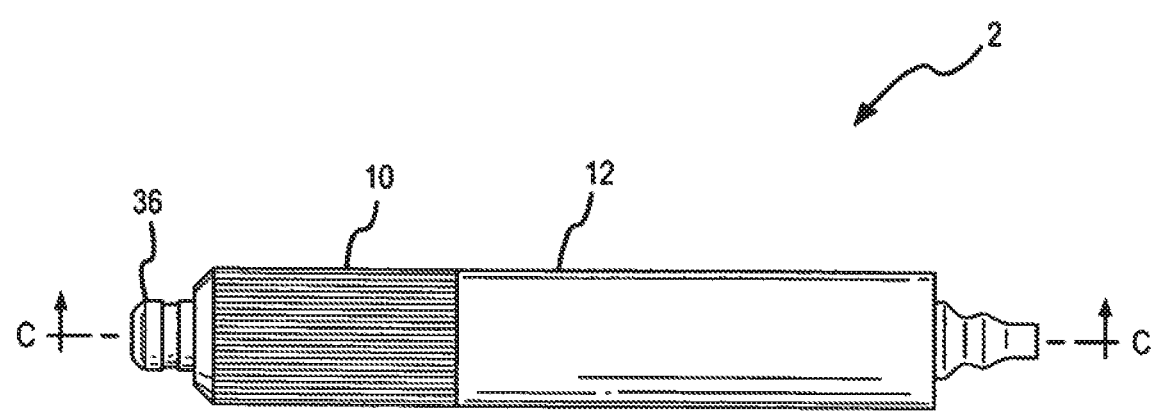
FIG. 7 is a plan view of another embodiment of the handle.
Figure 8:
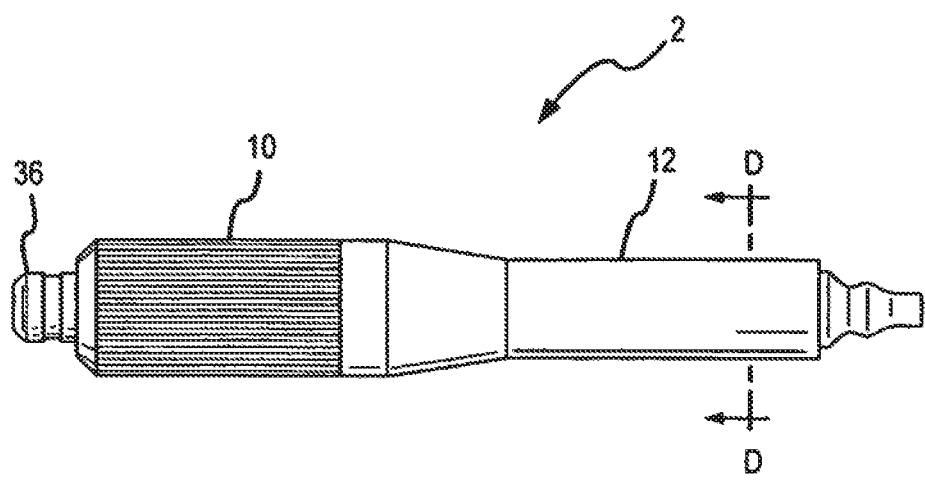
FIG. 8 is a side elevation of the handle depicted in FIG. 7.
Figure 9:
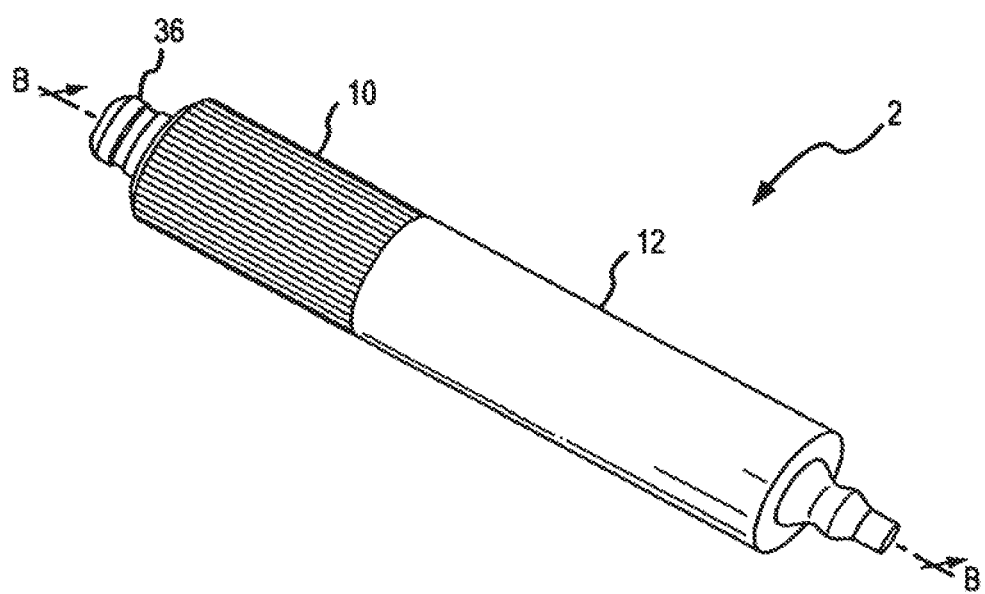
FIG. 9 is an isometric view of the distal end of the handle depicted in FIG. 7.

For a detailed discussion of another embodiment of the handle 2 of the present invention, reference is now made to FIGS. 7, 8 and 9. FIG. 7 is a plan view of the handle 2. FIG. 8 is a side elevation of the handle 2. FIG. 9 is an isometric view of the distal end of the handle 2.

As shown in FIGS. 7-9, the handle 2 includes an adjusting knob 10 on its distal end and a handle grip 12 on its proximal end. As can be understood from FIGS. 7-9, in one embodiment, the know 10 has a generally circular cross-section and the handle grip 12 has a generally oval cross-section. In one embodiment, both the know 10 and the handle grip 12 have generally circular cross-sections. The oval cross-section of the handle grip 12 is advantageous because it provides the physician with a tactile indication of the catheter's rotational position.

Figure 10:
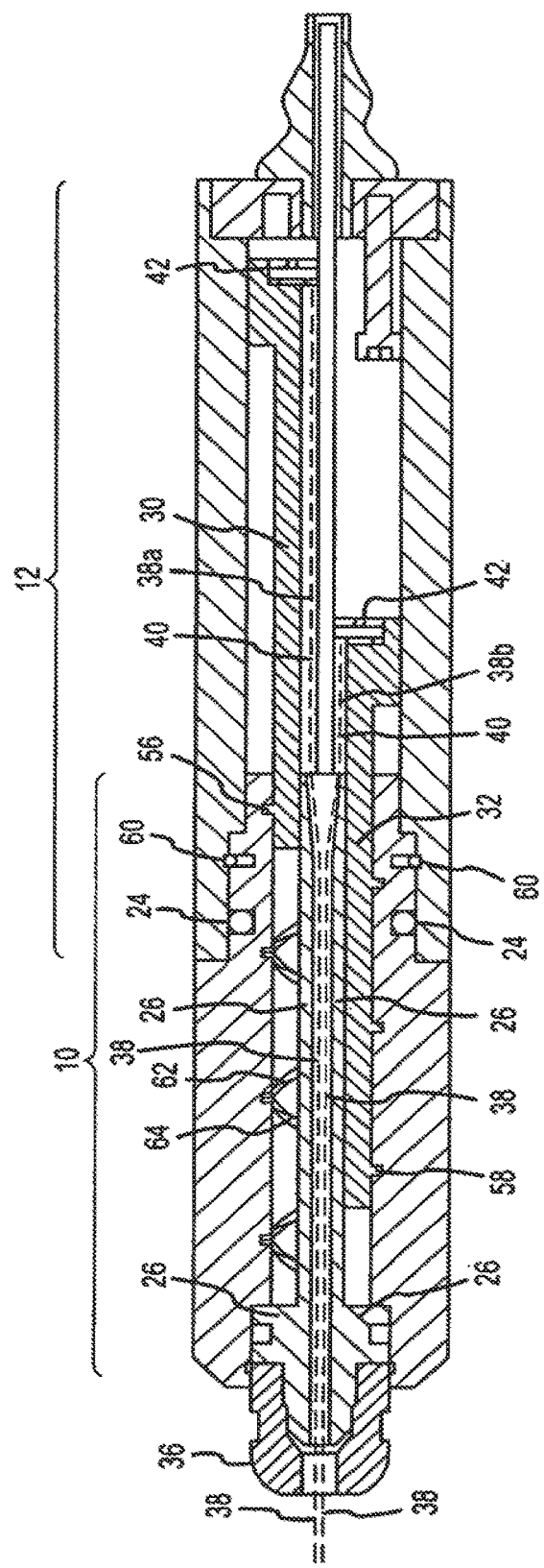
FIG. 10 is a longitudinal sectional plan view of the handle taken along section line BB of FIG. 9.

For a more detailed discussion of the components of the handle 2, reference is now made to FIG. 10, which is a longitudinal sectional plan view of the handle 2 taken along section line BB of FIG. 9. As shown in FIG. 10, an o-ring 24 is located between the handle grip 12 and a groove in the knob 10. The knob 10 is pivotally affixed to the handle grip 12 via rotating retaining-ring 60 that resides within grooves in both the knob and the handle grip 12.

Figure 11:
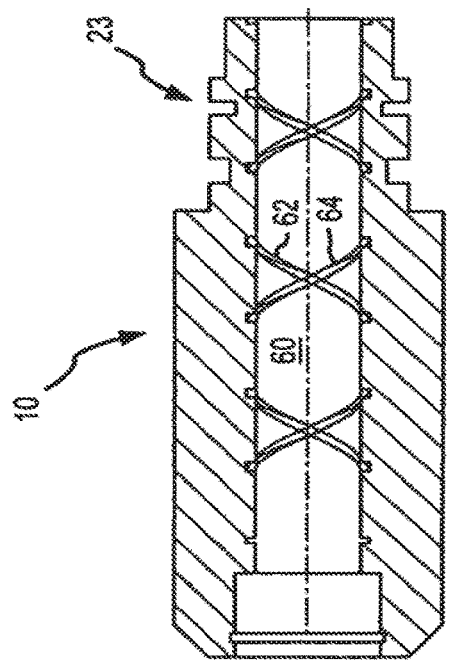
FIG. 11 is a longitudinal sectional plan view of the knob taken along section line BB in FIG. 9.

As illustrated in FIG. 10, a catheter body-retaining nut 36 is threadably affixed to the distal end of the wire guide 26 that extends along the axial center of the knob 10. As indicated in FIG. 10 and more clearly shown in FIG. 11, which is a longitudinal sectional plan view of the knob 10 taken along section line BB in FIG. 9, a cylindrical hole or shaft 60 passes through the knob 10 along the knob's longitudinal axis. The inner circumferential surface of the shaft 60 has both right hand threads 62 and left hand threads 64 that extend towards the distal end of the knob 10 from a hub portion 23 of the knob 10. As shown in FIG. 11, in one embodiment, the knob 10 is a singular integral piece.

Figure 12:
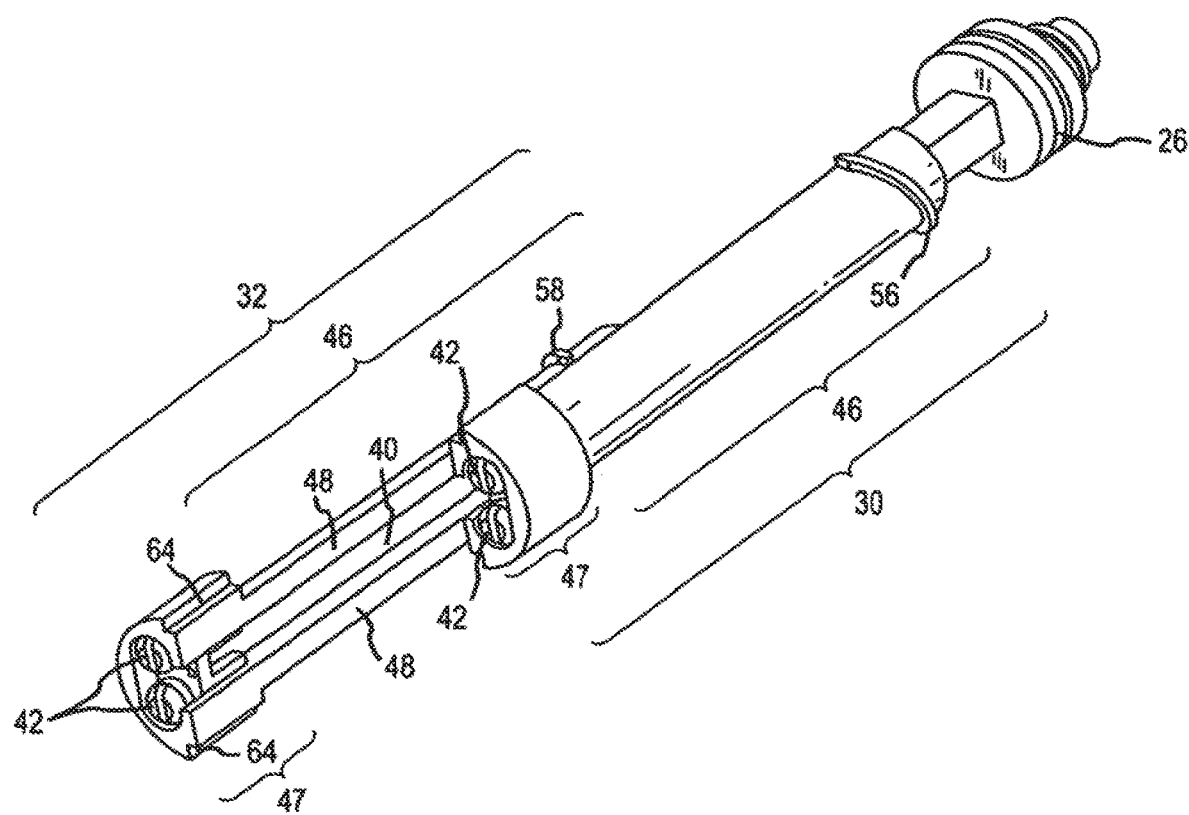
FIG. 12 is a right side isometric view of the slides displaced about the wire guide.
Figure 13:
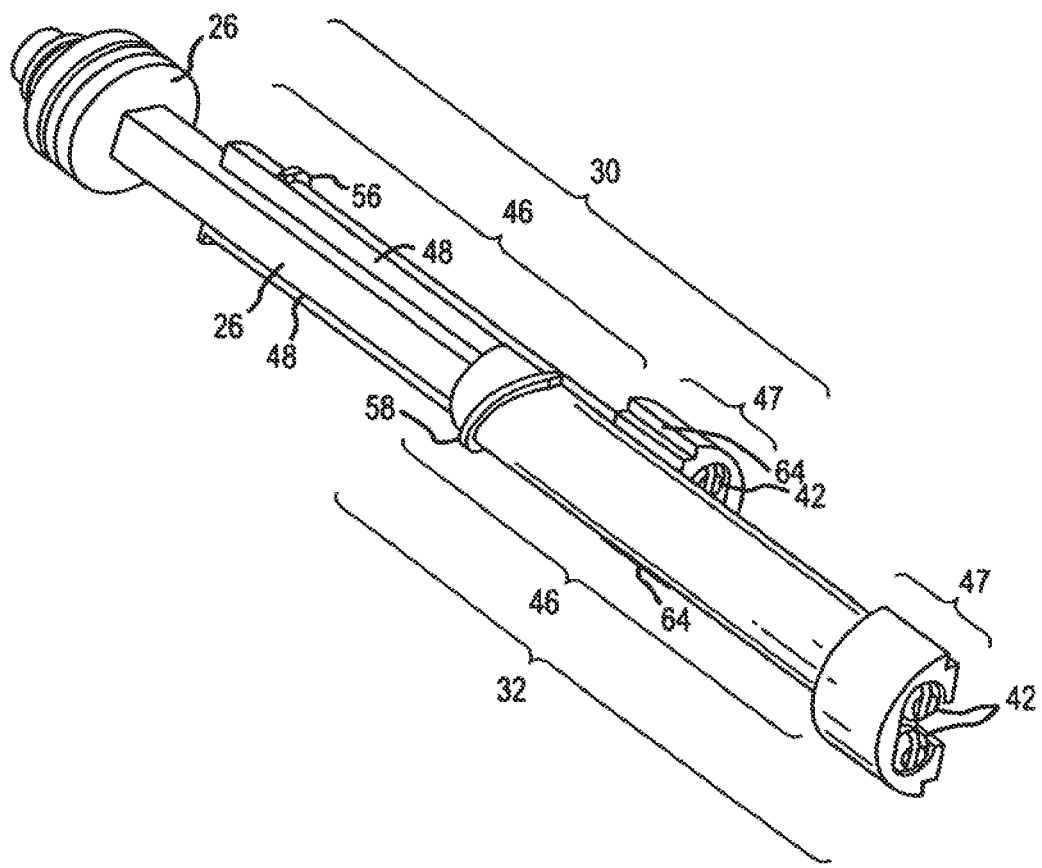
FIG. 13 is a left side isometric view of the slides displaced about the wire guide.

As indicated in FIG. 10, a right slide 30 and a left slide 32 are longitudinally displaceable within the handle 2 and about the proximal end of the wire guide 26. As shown in FIGS. 12 and 13, which are, respectively, a right side isometric view of the slides 30, 32 displaced about the wire guide 26 and a left side isometric view of the slides 30, 32 displaced about the wire guide 26, each slide 30, 32 has a planar slide face 48 that abuts and slideably displaces against the slide face 48 of the opposed slide 30, 32. Also, each slide 30, 32 has a channel 40 that combines with the channel 40 of the opposed slide 30, 32 to form a passage 40 through which the proximal end of the wire guide 26 passes as the slides 30, 32 displace about the wire guide 26. As shown in FIG. 10, the passage 40 formed by the channels 40 also provides a pathway along which the deflection wires 38a, 38b (represented by dashed lines in FIG. 10) travel from a proximal portion of the slides 30, 32, through the wire guide 26, and onward to the extreme distal end 14 of the catheter body 4.

As indicated in FIGS. 12 and 13, each slide 30, 32 has a half-cylinder distal portion 46 and a shorter and wider half-cylinder proximal portion 47. The right slide 30 has a right-handed thread 56 on its distal portion 46. Similarly, the left slide 32 has a left-handed thread 58 on its distal portion 46. Thus, as can be understood from FIG. 10, when the knob 10 is rotated in a clockwise direction relative to the handle grip 12, the right handed threads 62 within the knob 10 engage the right handed threads 56 of the right slide 30, and the left handed threads 64 within the knob 10 engage the left handed threads 58 of the left slide 32. As a result, the right slide 30 is distally displaced within the handle 2 and the left slide 32 is proximally displaced within the handle 2. Accordingly, the deflection wire 38a attached to the right slide 30 is pushed (i.e., subjected to a compressive force) and the deflection wire 38b attached to the left slide 32 is pulled (i.e., subjected to a tension force). Conversely, if the knob is rotated counterclockwise, the opposite displacement of the slides 30, 32 and deflection wires 38a, 38b will occur.

As indicated in FIG. 10, each deflection wire 38a, 38b is attached to the proximal portion 47 of its respective slide 30, 32 via retention screws 42. The retention screws, which are more clearly illustrated in FIGS. 12 and 13, are threadably mounted in the proximal portions 47.

As shown in FIGS. 12 and 13, each half-cylindrical proximal portion 47 of a slide 30, 32 has an upper and lower planar notch 64 adjacent their respective planar slide faces 47. The function of these notches 64 may be understood by referring to FIGS. 14 and 15.

Figure 14:
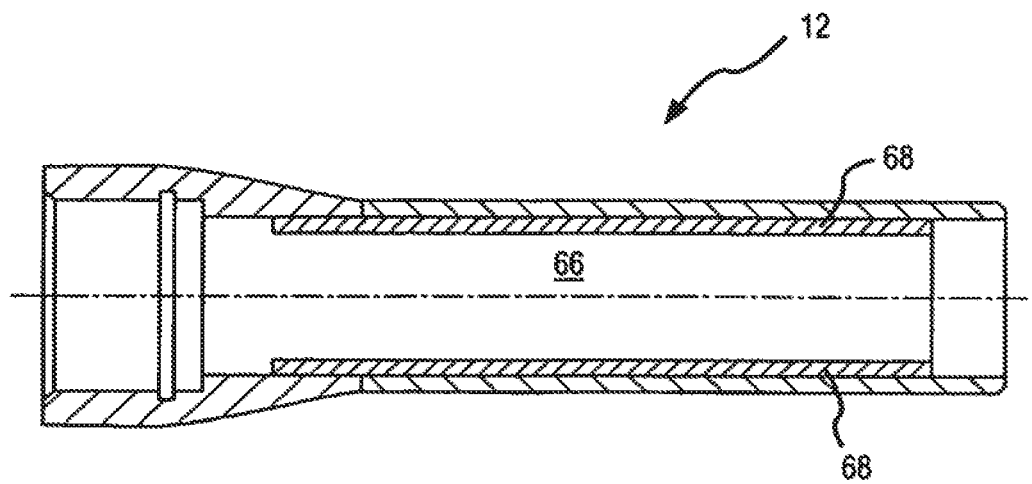
FIG. 14 is a longitudinal sectional elevation of the handle grip taken along section line CC in FIG. 7.
Figure 15:
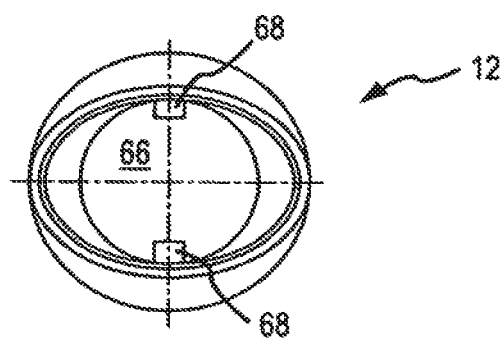
FIG. 15 is a latitudinal sectional elevation of the handle grip taken along section line DD in FIG. 8.

FIG. 14 is a longitudinal section elevation of the handle grip 12 taken along section line CC in FIG. 7. FIG. 15 is a latitudinal section elevation of the handle grip 12 taken along section line DD in FIG. 8. As shown in FIGS. 14 and 15, the handle grip 12 is one integral piece having an indicated in FIG. 10.

As shown in FIGS. 14 and 15, upper and lower ribs 68 extend from the walls that form the interior cylindrical void 66. The ribs 68 run longitudinally along a substantial portion of the cylindrical void's length. As can be understood from FIGS. 12-15, the upper planar notches 64 on the proximal portions 47 of the slides 30, 32 interface with, and displace along, the upper rib 68 as the slides 30, 32 displace within the cylindrical void 66. Similarly, the lower planar notches 64 on the proximal portions 47 of the slides 30, 32 interface with, and displace along, the lower rib 68 as the slides 30, 32 displace within the cylindrical void 66. Thus, the ribs 68 act as thrust surfaces for the slides 30, 32.

Figure 16:
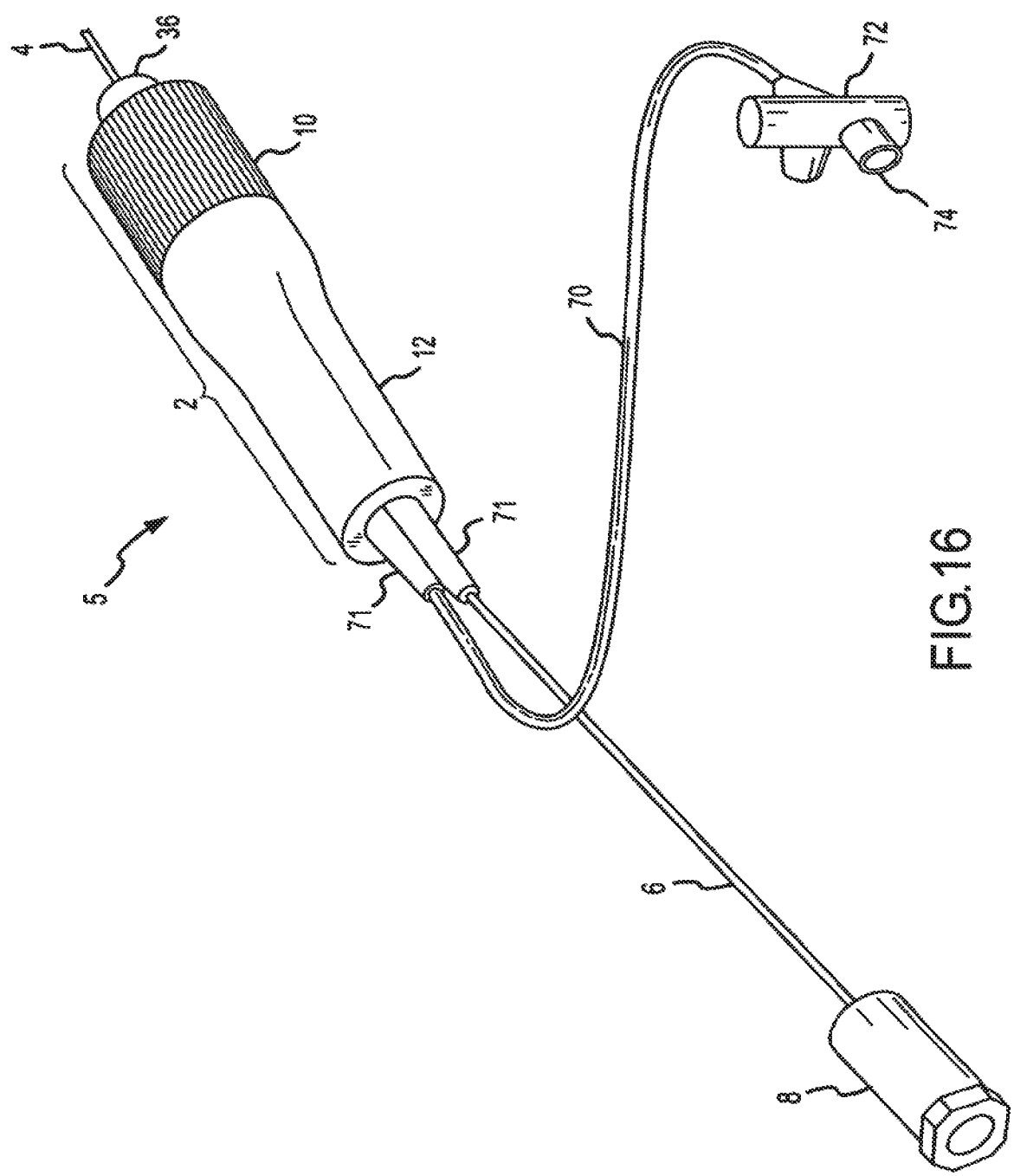
FIG. 16 is an isometric view of the distal end of a control handle for a catheter wherein the handle has a through lumen.

For a detailed discussion of another embodiment of the handle 2 depicted in FIGS. 7-15, reference is now made to FIG. 16. FIG. 16 is an isometric view of the distal end of a control handle 2 for a catheter 5 wherein the handle 2 and catheter body 4 have a through lumen 70. As shown in FIG. 16, in one embodiment, the lumen 70 and the electrical wire tube 6, which extends to the electrical connector 8, pass through strain reliefs 71 and into the proximal end of the handle grip 12. In one embodiment, the lumen 70 terminates at its proximal end with a stopcock 72. In one embodiment, the stopcock 72 has a hemostasis seal 74 that can be utilized for guide wire insertion. While a long flexible length of lumen 70, as depicted in FIG. 16, provides motion isolation while inserting contrast from a syringe, in one embodiment, the lumen 70 does not extend from the handle grip 12. Instead, the stopcock 72 or luer fitting is simply attached to the lumen 70 where it exits the proximal end of the handle grip 12.

Figure 17:
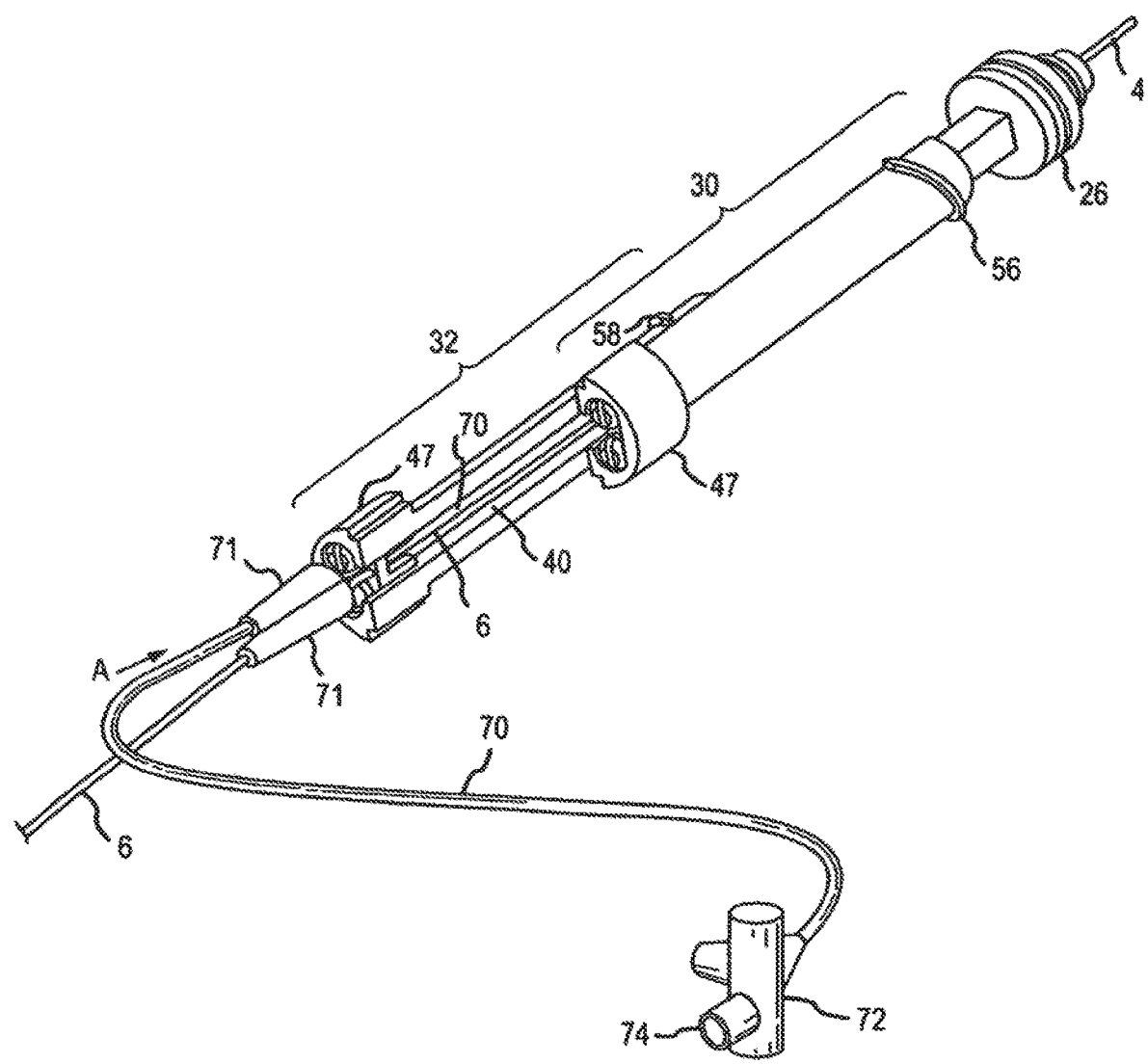
FIG. 17 is an isometric view of the slides, the wire guide, the wire tubing, and the lumen illustrating the path the lumen takes through the handle.
Figure 18:
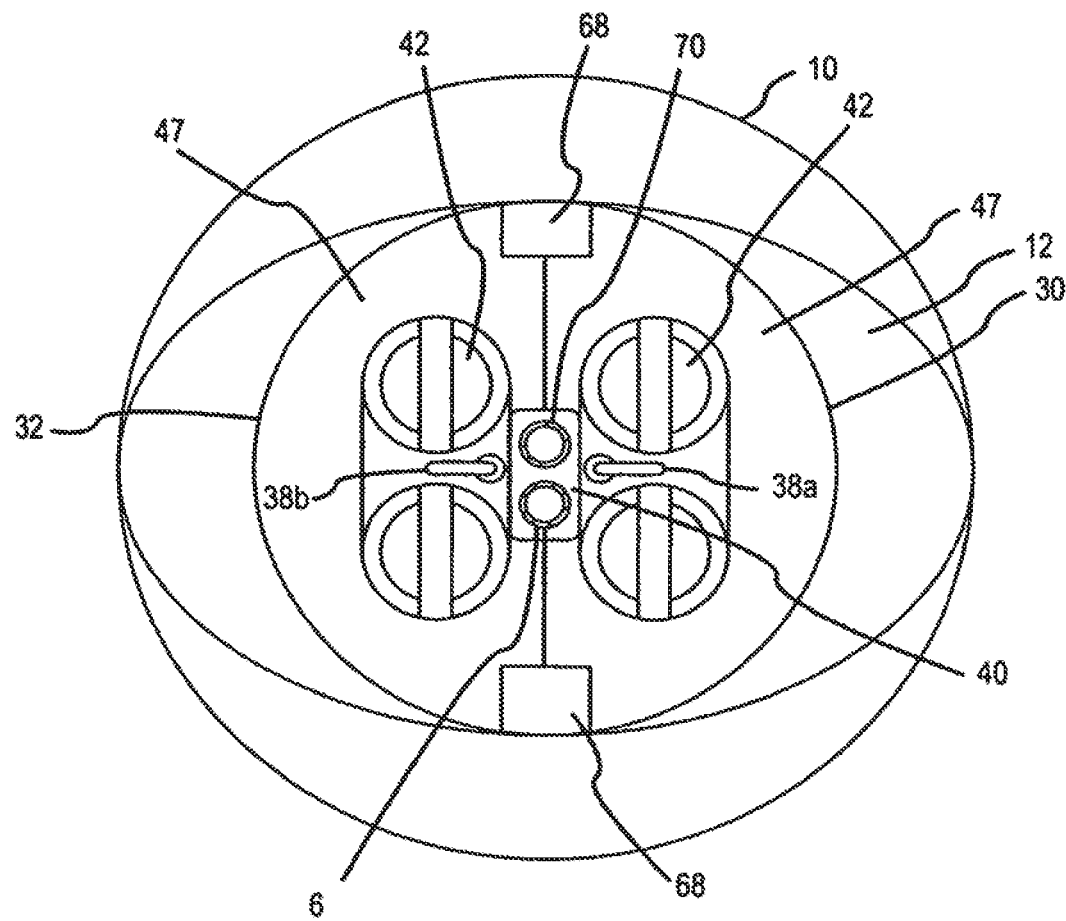
FIG. 18 is an elevation view of the extreme proximal end surfaces of the slides as viewed from allow A in FIG. 17 and illustrating the path the lumen and wire tubing take into the passage formed by the channels of the slides.
Figure 19:
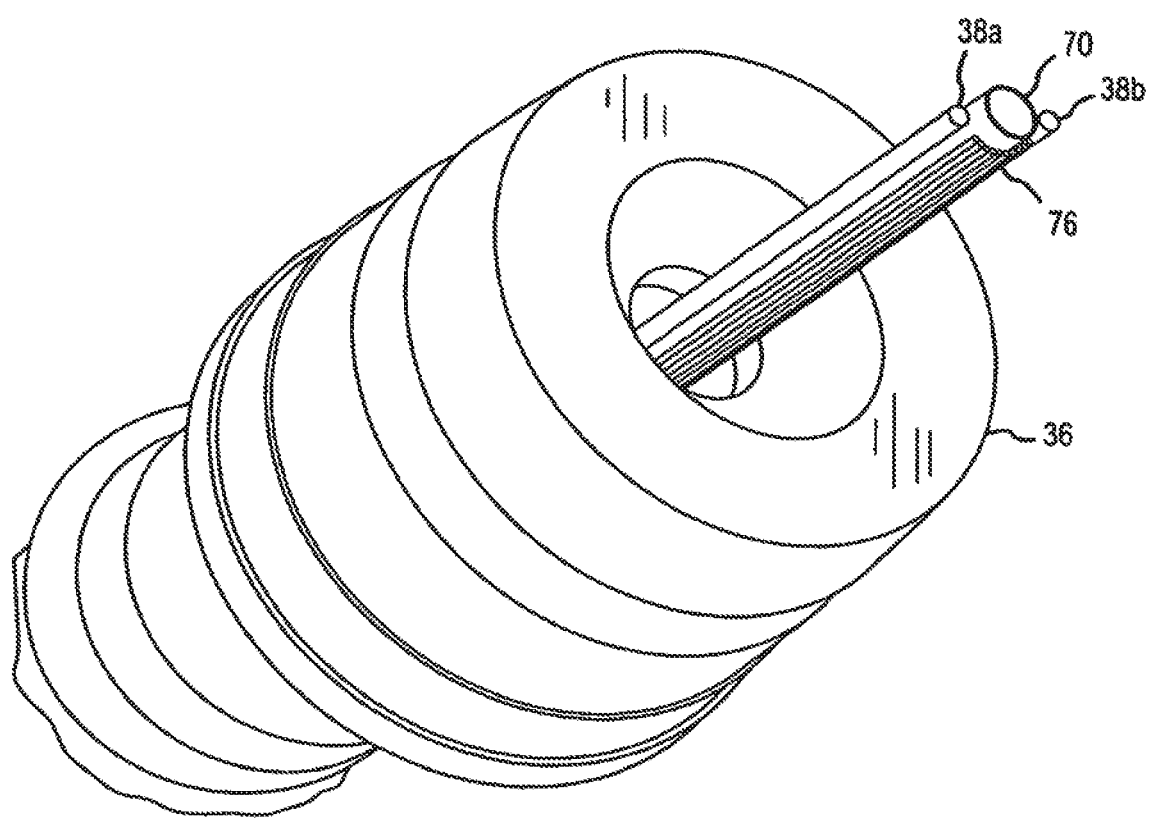
FIG. 19 is an isometric view of the lumen, deflection wires, and electrical wires of the tube exiting the catheter body-retaining nut on the distal end of the handle.

For a better understanding of the path of the lumen 70, reference is now made to FIGS. 17, 18 and 19. FIG. 17 is an isometric view of the slides 30, 32, the wire guide 26, the wire tubing 6, and the lumen 70 illustrating the path the lumen 70 takes through the handle 2. FIG. 18 is an elevation view of the extreme proximal end surfaces of the slides 30, 32 as viewed from arrow A in FIG. 17 and illustrating the path the lumen 70 and wire tubing 6 take into the passage 40 formed by the channels 40 of the slides 30, 32. FIG. 19 is an isometric view of the lumen 70, deflection wires 38a, 38b, and electrical wires 76 of the wire tube 6 exiting the catheter body-retaining nut 36 on the distal end of the handle 2.

As shown in FIGS. 17 and 18, the lumen 70 and the wire tubing 6 pass through their respective reliefs 71 and into the passage 40 formed by the channels 40 in each slide 30, 32. In one embodiment, soon after the wire tubing 6 and the lumen 70 enter the passage 40, the wires 76 of the wire tubing 6 exit the wire tubing 6 and are dispersed about the outer circumference of the lumen 70 as depicted in FIG. 19.

As illustrated in FIG. 17, in another embodiment, after the wire tube 6 and lumen 70 enter the passage 40, the wire tube 6 and the lumen 70 continue on their pathway to the distal end 14 of the catheter body 4 by passing, in a side-by-side arrangement, through the remainder of the passage 40 formed into the slides 30, 32 and into an internal passage that extends along the longitudinal axis of the wire guide 26. Near the end of the wire guide 26, the wire 76 exists the wire tube 6. The wire 76, lumen 70 and deflection wires 38a, 38b then pass into the catheter by exiting the catheter body-retaining nut 36 of the handle as indicated in FIG. 19.

Figure 20:
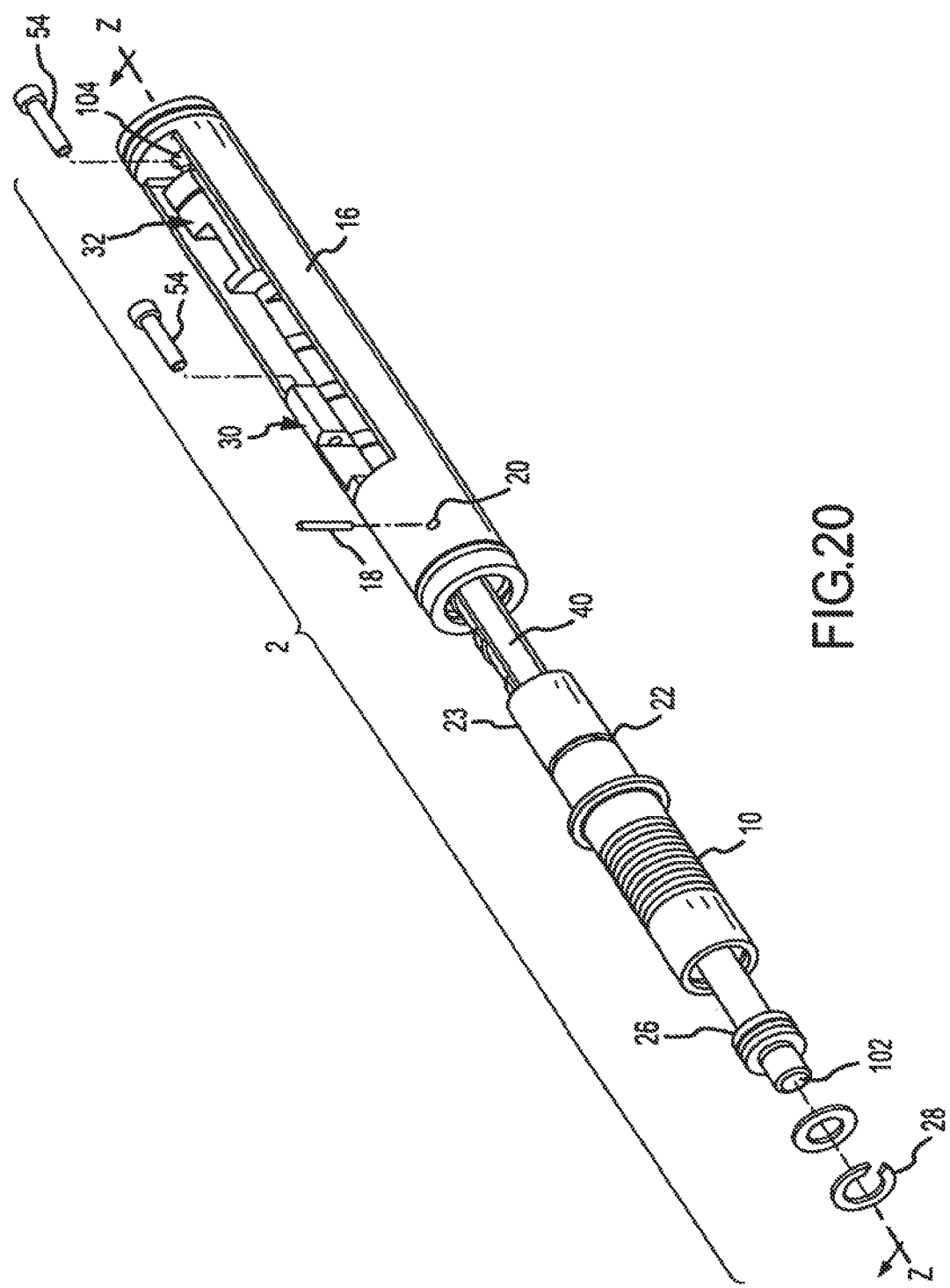
FIG. 20 is an isometric view of another embodiment of the handle exploded to show its various components.

For detailed discussion of another embodiment of the handle 2, reference is now made to FIG. 20, which is an isometric view of the handle 2 exploded to show its various components. As can be understood from FIG. 20, the features of the handle 2 depicted in FIG. 20 are similar to the features of the handle depicted in FIG. 2, except the handle 2 depicted in FIG. 20 is configured to have a relatively large, generally uniform in diameter, pathway extend the full length of the handle 2 (i.e., from the distal opening 102 in the wire guide 26, through the passage 40 defined in the slides 30, 32 and through an exit hole 104 in the proximal end of the shaft 16).

The configuration of the handle 2 that allows a relatively large generally uniform in diameter pathway to pass through the length of the handle 2, as depicted in FIG. 20, is more clearly shown in FIG. 21, which is a longitudinal sectional elevation taken along section line ZZ in FIG. 20. As illustrated in FIG. 21, in one embodiment, the pathway 100, which includes the passage through the wire guide 26 and the passage 40 through the slides 30, 32, is large enough that the catheter body 4 itself may pass through the pathway 100 and be connected to the proximal end of the shaft 16 at the exit hole 104. Thus, in one embodiment, to prevent the catheter body 4 from rotating with the adjusting knob 10, the catheter body 4 is affixed to the shaft 16 at the exit hole 104. In one embodiment, the catheter body 4 runs the full length of the handle 4 as depicted in FIG. 21, except the body 4 is affixed to the wire guide 26 at or near the distal opening 102. In other embodiments, the catheter body 4 is affixed to both the wire guide 26 at or near the distal opening 102 and the shaft 16 at the exit hole 104.

As can be understood from FIG. 21 and as more clearly depicted in FIG. 22, which is isometric views of the slides 30, 32 oriented to show their portions of the passage 40 and their planar slide faces 48, the passage 40 is large enough in diameter to displace over the outer diameter of the wire guide 26. As shown in FIGS. 21 and 22, a catheter body passage 110 passes through the proximal portion 44 of each slide 30, 32, thereby allowing the slides 30, 32 to displace back and forth over the outer surface of the catheter body 4.

As indicated in FIG. 21, in one embodiment, the catheter body 4 has an opening 111 in its wall that allows the wires 38 to exit the body 4 and connect to the slides 30, 32. In one embodiment, the wires 38 connect to the slides 30, 32 via tension adjustment screws 54 as previously discussed.

Due to the configuration of the slides 30, 32, the wire guide 26 and the shaft 16, the catheter body 4 may run uninterrupted the full length of the handle 2. As a result, electrical wiring 76 (see FIG. 19) and a lumen 70 may be routed the full length of the handle 2 by way of the body 4.

Figure 23:
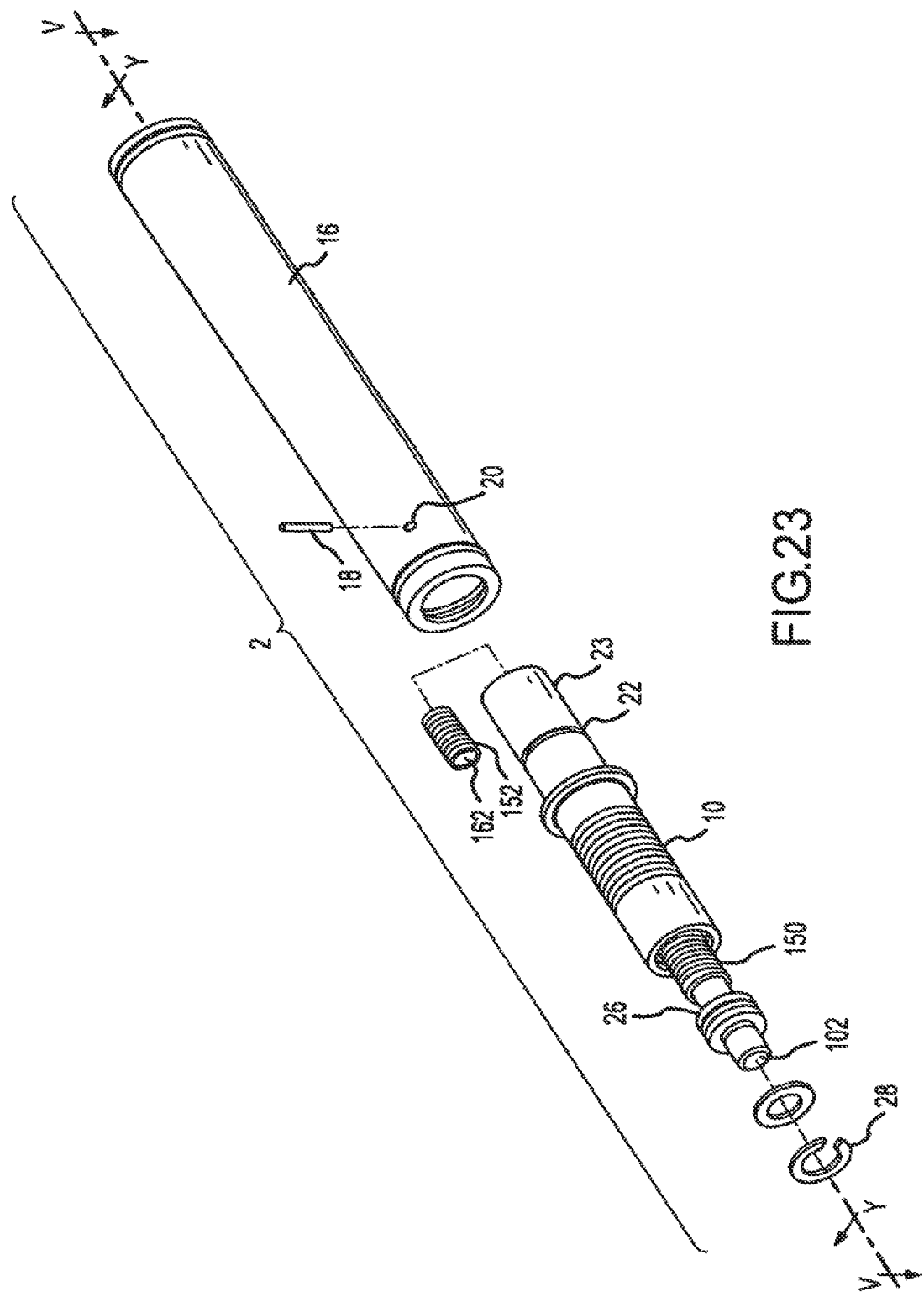
FIG. 23 is an isometric view of another embodiment of the handle exploded to show its various components.
Figure 24:
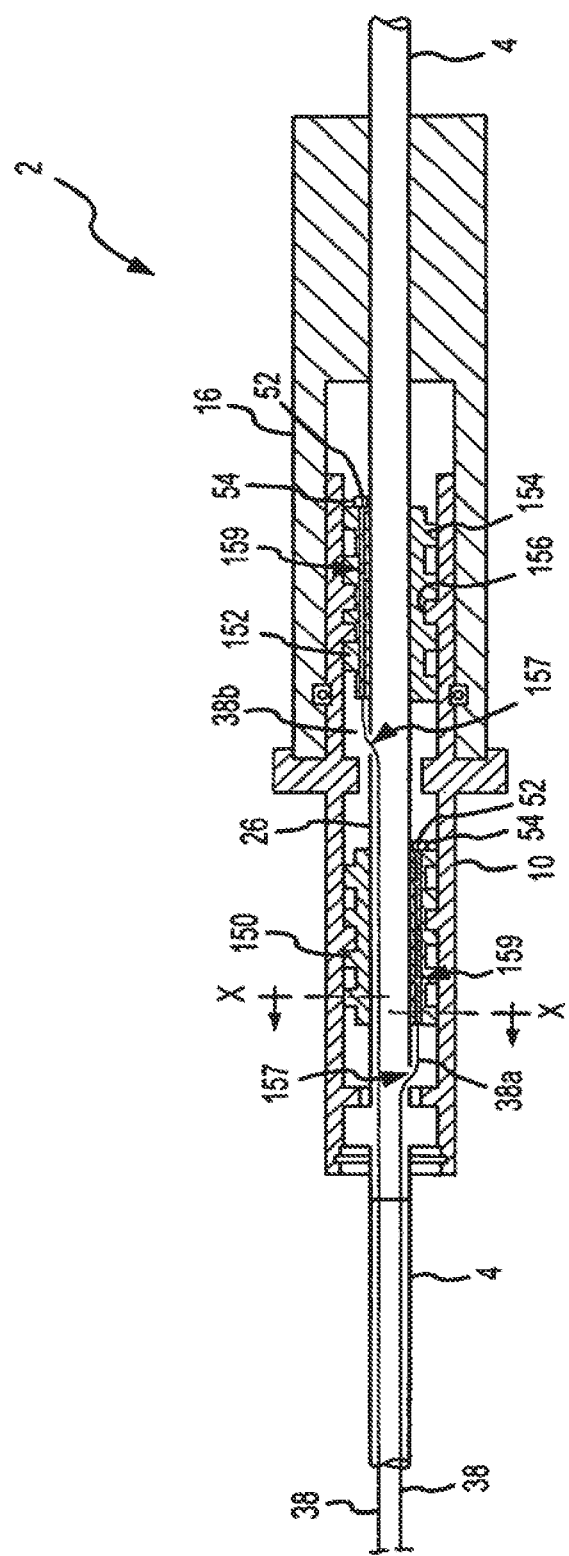
FIG. 24 is a longitudinal sectional elevation of the handle taken along section line YY of FIG. 23.

For a detailed discussion of another embodiment of the handle 2 of the present invention, reference is now made to FIGS. 23 and 24. FIG. 23 is an isometric view of the handle 2 exploded to show its various components. FIG. 24 is a longitudinal sectional elevation of the handle 2 taken along section lone YY of FIG. 23. Generally speaking, the features of the handle 2 depicted in FIGS. 23 and 24 are similar to the features of the handle depicted in FIG. 20, except the two embodiments employ different slider arrangements. For example, the embodiments depicted in FIGS. 1-22 employ parallel slides or members 30, 32 (i.e., the slides 30, 32 exist within the handle 2 in a parallel or side-by-side arrangement). As will be understood from FIGS. 23 and 24 and the following figures, in the embodiment of the handle 2 depicted in FIGS. 23 and 24, the slides or members 150, 152 exist within the adjustment knob 10 in a series arrangement (i.e., the slides 150, 152 are not parallel or side-by-side to each other, but are oriented end-to-end along a longitudinal axis of the handle 2).

As shown in FIGS. 23 and 24, the adjusting knob 10 is pivotally coupled to the distal end of the mounting shaft (i.e., base portion) 16. The wire guide 26 extends through the center of the adjusting knob 10 and the mounting shaft 16. The catheter body 4 is coupled to the distal end of the wire guide 26 and, in one embodiment, extends through the wire guide 26 and out of the proximal end of the mounting shaft 16.

As shown in FIGS. 23 and 24, a distal slide 150 is located in a distal portion of the adjusting knob 10, and a proximal slide 152 is located in a proximal portion (i.e., hub portion 23) of the adjusting knob 10. As illustrated in FIG. 24, the outer surface of each slide 150, 152 has threads 154 that mate with threads 156 on an interior surface of the adjusting knob 10.

As illustrated in FIG. 24, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in this Detailed Description.

Figure 25:
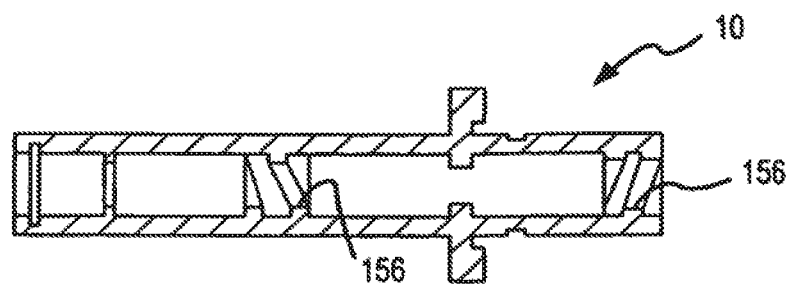
FIG. 25 is the same longitudinal sectional elevation of the adjusting knob as depicted in FIG. 24, except the adjusting knob is shown by itself.
Figure 26:
FIG. 26 is a side elevation of the slides.

For a better understanding of the orientation of the threads 154, 156, reference is now made to FIGS. 25 and 26. FIG. 25 is the same longitudinal sectional elevation of the adjusting knob 10 as it is depicted in FIG. 24, except the adjusting knob 10 is shown by itself. FIG. 26 is a side elevation of the slides 150, 152.

As shown in FIGS. 25 and 26, in one embodiment, the distal slide 150 has right hand threads 154 that engage right hand threads 156 in the distal portion of the adjusting knob 10, and the proximal slide 152 has left hand threads 154 that engage left hand threads 156 in the proximal portion of the adjusting knob 10. Thus, as can be understood from FIGS. 23-26, when the adjusting knob 10 is rotated relative to the mounting shaft 16 in a first direction about the longitudinal axis of the handle 2, the slides 150, 152 will converge along the wire guide 26, thereby causing the first wire 38 to be placed into tension and the second wire 38 to be compressed. As a result, the distal end 14 of the catheter body 4 will deflect in a first direction. Similarly, when the adjusting knob 10 is rotated in a second direction that is opposite from the first direction, the slides 150, 152 will diverge along the wire guide 26, thereby causing the first wire 38 to be compressed and the second wire 38 to be placed into tension. As a result, the distal end 14 of the catheter body 4 will deflect in a second direction generally opposite from the first direction.

Figures 27A, 27B:
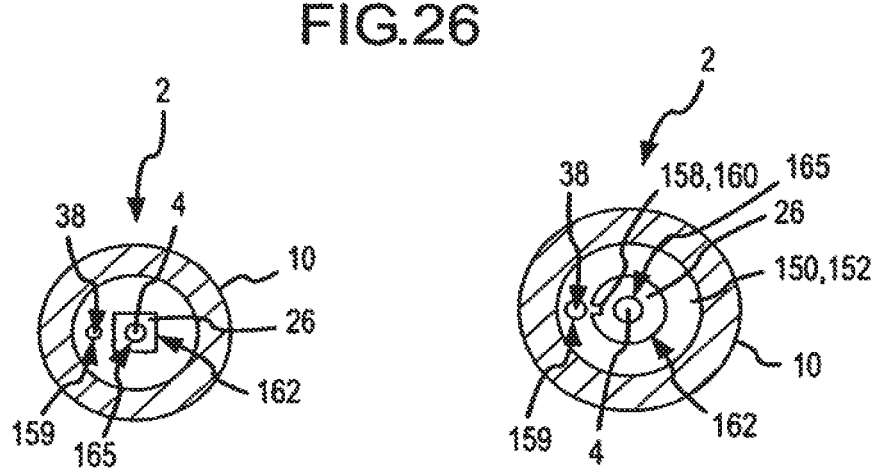
FIG. 27A is a latitudinal sectional elevation of the handle, as taken along section line XX in FIG. 24, wherein the wire guide has a square cross section.
FIG. 27B is the same latitudinal sectional elevation depicted in FIG. 27A, except the wire guide has a circular cross section and a key/groove arrangement.

In one embodiment, to prevent the slides 150, 152 from simply rotating around the wire guide 26 when the adjusting knob 10 is rotated, the slides 150, 152 and wire guide 26 are configured such that the slides 150, 152 will displace along the wire guide 26, but not rotationally around it. For example, as indicated in FIG. 27A, which is a latitudinal sectional elevation of the handle 2 as taken along section line XX in FIG. 24, the wire guide 26 has a square cross section that mates with a square hole 162 running the length of the slide 150, 152. The interaction between the square hole 162 and the square cross section of the wire guide 26 prevents a slide 150, 152 from rotation about the wire guide 26, but still allows the slide 150, 152 to displace along the length of the wire guide 26.

Figure 28:
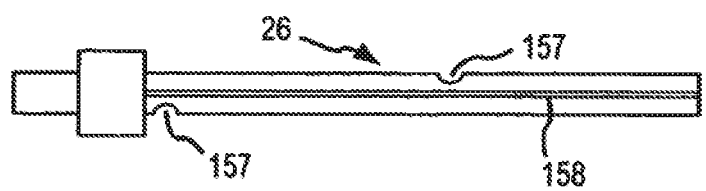
FIG. 28 is a side elevation of one embodiment of the wire guide equipped with a groove.

In another embodiment, as shown in FIG. 27B, which is the same latitudinal sectional elevation depicted in FIG. 27A, each slide 150, 152 has a hole 162 with a circular cross section. Each hole 162 runs the length of its respective slide 150, 152 and includes a key 160 that extends into the hole 162 from the interior circumferential surface of the hole 160. The key 160 engages a groove or slot 158 that runs along the length of the wire guide 26 as depicted in FIG. 28, which is a side elevation of one embodiment of the wire guide 26. The interaction between the key 160 and the slot 158 prevents a slide 150, 152 from rotating about the wire guide 26, but still allows the slide 150, 152 to displace along the length of the wire guide 26.

As shown in FIGS. 27A and 27B, a hollow shaft 165 extends through the wire guide 26. This allows a catheter body 4 with a lumen to extend completely through the handle 2 as shown in FIG. 24.

For a detailed discussion of another embodiment of the handle 2 that is similar to the embodiment depicted in FIG. 23, reference is now made to FIGS. 29 and 30. FIG. 29 is a longitudinal sectional elevation of the handle 2 as if taken through section line YY of FIG. 23. FIG. 30 is a longitudinal sectional plan view of the handle 2 as if taken through section line VV in FIG. 23 and wherein section line VV forms a plane that is perpendicular to the plane formed by section line YY in FIG. 23.

As illustrated in FIGS. 29 and 30, the handle 2 includes an adjusting knob 10 pivotally coupled to the distal end of the mounting shaft (i.e., base portion) 16. In one embodiment, the adjusting knob 10 includes a proximal end 170, a distal end 172 and a threaded shaft 173, which is connected to the proximal end 170 and extends distally along the longitudinal axis of the adjusting knob 10. The threaded shaft 173 includes a distal end 174, a proximal end 176, a series of right hand threads 178 along a distal portion of the shaft 173, and a series of left hand threads 180 along a proximal portion of the shaft 173.

As shown in FIGS. 29 and 30, a distal slide 150 is located in a distal portion of the adjusting knob 10, and a proximal slide 152 is located in a proximal portion (i.e., hub portion 23) of the adjusting knob 10. Each slide has a hole 155 through which the threaded shaft 173 passes. The inner circumferential surface of the hole 155 for the distal slide 150 has right hand threads that mate with the right hand threads 178 on the distal portion of the shaft 173. Similarly, the inner circumferential surface of the hole 155 for the proximal slide 152 has left hand threads that mate with the left hand threads 180 on the proximal portion of the shaft 173. In other embodiments, the locations for the left and right threads are reversed.

As can be understood from FIGS. 29, 30 and 31, which is an isometric view of one embodiment of the wire guide 26, a hollow center shaft 182 extends from the distal end of the wire guide 26, through the threaded shaft 173 of the adjustment knob 10, and to the proximal end of the base shaft 16. Thus, in one embodiment, a catheter body 4 may be routed through the lumen 165 of the wire guide's hollow center shaft 182 to exit the proximal end of the handle 2, as illustrated in FIGS. 29 and 30.

As illustrated in FIG. 29, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through 159 in the slide 150, 152 and attaches to a hollow tension adjustment screw 54 via a knot 52 as previously described in this Detail Description.

In one embodiment, as shown in FIG. 29, the deflection wire 38b leading to the proximal slide 152 passes through a second passage 161 in the distal slide 150. The second passage 161 has sufficient clearance that the passage 161 may easily displace along the wire 38b when the distal slide 150 displaces distally and proximally. The second passage 161 serves as a guide that stiffens the wire 38b and helps to reduce the likelihood that the wire 38b will bend when compressed.

As can be understood from FIGS. 29 and 30, when the adjusting knob 10 is rotated relative to the mounting shaft 16 in a first direction about the longitudinal axis of the handle 2, the slides 150, 152 will converge along the threaded shaft 173, thereby causing the first wire 38a to be placed into tension and the second wire 38b to be compressed. As a result, the distal end 14 of the catheter body 4 will deflect in a first direction. Similarly, when the adjusting knob 10 is rotated in a second direction that is opposite from the first direction, the slides 150, 152 will diverge along the threaded shaft 173, thereby causing the first wire 38a to be compressed and the second wire 38b to be placed into tension. As a result, the distal end 14 of the catheter body 4 will deflect in a second direction generally opposite from the first direction.

In one embodiment, to prevent the slides 150, 152 from simply rotating with the threaded shaft 173 within the adjusting knob 10 when the adjusting knob 10 is rotated, the slides 150, 152 and wire guide 26 are configured such that the slides 150, 152 will displace along the threaded shaft 173, but not rotationally within the adjusting knob 10. For example, as indicated in FIGS. 31 and 32, which is a latitudinal sectional elevation of the handle 2 as taken along section line WW in FIG. 29, the wire guide 26 has right and left semicircular portions 190 that oppose each other and extend along the length of the hollow center shaft 182 of the wire guide 26. As shown in FIG. 32, the generally planar opposed faces 192 of the semicircular portions 190 abut against the generally planar side face 194 of the slides 150, 152. This interaction prevents a slide 150, 152 from rotating within the adjustment knob 10 when the knob 10 is rotated, but still allows the slide 150, 152 to displace along the length of the threaded shaft 173.

As can be understood from FIG. 36, which is diagrammatic illustration of the control handle 2 of the subject invention being employed in a surgical procedure on a patient 200, the distal end 14 of the catheter body 4 is inserted into the patient 200 (e.g., intravenously via a body lumen 202 of the patient 200, percutaneously, or via other avenues for entering the patient's body). The distal end 14 of the catheter body 4 is advanced until positioned in a selected location within the patient 200 (e.g., within a chamber 204 of the patient's heart 206 or other organ, with a body cavity of the patient, etc.). The distal end of the catheter body 4 is then deflected by rotating the adjustment knob 10 about a longitudinal axis of the base portion 16. As can be understood from FIGS. 1-35, this causes the slides 30, 32 within the handle 2 to displace along the longitudinal axis in opposite directions. Since each slide 30, 32 is coupled to its respective deflection wire 38 and each deflection wire 38 runs through the catheter body 4 and is coupled to the distal end 14, the distal end 14 of the catheter body 4 is deflected.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus comprising:
a handle with a handle outer surface and having a longitudinal axis;
an adjustment knob coupled to the handle wherein the adjustment knob has a knob outer surface, said adjustment knob being rotatable about the longitudinal axis;
an flexible elongate member having a distal end portion and a proximal portion, wherein the proximal portion is coupled to the handle;
first and second elongate deflection members operatively coupled to the adjustment knob and to the distal end portion of the flexible elongate member; and
means disposed within the handle and operatively coupled to the adjustment knob for simultaneously imparting a tensile force to one of the first and second deflection members and releasing a tensile force on the other one of the first and second deflection members, wherein the means for simultaneously imparting includes a threaded shaft with first threads connected to the adjustment knob for rotation therewith and a slide having second threads that mate with the first threads;
wherein the slide is coupled to at least one of the first and second deflection members, and wherein rotation of the adjustment knob rotates the threaded shaft to displace the slide along a length of the threaded shaft such that the distal end portion of the flexible elongate member deflects from a first configuration to a second configuration; and
wherein the handle outer surface and the knob outer surface are substantially unchanged when the flexible elongate member is disposed in the first and second configurations.

2. The apparatus of claim 1 wherein rotation of the adjustment knob rotates the threaded shaft, causing movement of the first and second deflection members in opposite directions.

3. The apparatus of claim 1 wherein the handle includes one of generally oval and circular cross-sections.

4. The apparatus of claim 1 wherein the adjustment knob includes a generally circular cross-section.

5. The apparatus of claim 1 wherein rotation of the adjustment knob imparts the tensile force to the at least one of the first and second deflection members by linear movement of the slide relative to the adjustment knob.

6. The apparatus of claim 1 further comprising a lumen extending through the flexible elongate member terminating at an external opening at the distal end portion of the flexible elongate member.

7. The apparatus of claim 6 wherein the lumen is sized and configured to receive a medical device and said external opening is axially oriented.

8. The apparatus of claim 7 wherein the medical device comprises a catheter for delivering or receiving energy.

9. The apparatus of claim 1 wherein the first and second deflection members each comprises one of a pull wire, a filament, a braided cord, and a resin-based member.

10. The apparatus of claim 1 wherein the adjustment knob is operably coupled to one of an intermediate body portion and a distal portion of the handle.

11. The apparatus of claim 1 further comprising a hemostasis valve coupled to the handle.

12. The apparatus of claim 1 wherein the slide is a first slide, the simultaneously imparting means further including a second slide, wherein the first and second slides comprise a pair of generally axially displaceable members disposed within the handle, wherein rotation of the adjustment knob imparts opposing forces to the axially displaceable members.

13. The apparatus of claim 1 further comprising at least one electrode coupled to the flexible elongate member.

14. The apparatus of claim 1 wherein the flexible elongate member comprises a biocompatible electrically insulative material.

15. The apparatus of claim 1 further comprising at least one reinforcing element disposed within a portion of the flexible elongate member.

16. The apparatus of claim 15 wherein the reinforcing element comprises braided members.

17. The apparatus of claim 1 wherein in the first configuration, the distal end portion of the flexible elongate member is substantially straight.

18. The apparatus of claim 1 further comprising an anchor ring coupled to the distal end portion of the flexible elongate member, wherein the first and second elongate deflection members comprise at least first and second elongate pull wires coupled to the anchor ring.

19. An apparatus comprising:
a handle with a handle outer surface and having a longitudinal axis;
an adjustment knob coupled to the handle wherein the adjustment knob has a knob outer surface, said adjustment knob being rotatable about the longitudinal axis;
a flexible tubular body having a distal end portion and a proximal portion, wherein the proximal portion is coupled to the handle;
first and second deflection wires operatively coupled to the adjustment knob and to the distal end portion of the flexible tubular body; and
means disposed within the handle and operatively coupled to the adjustment knob for simultaneously imparting a tensile force to one of the first and second deflection wires and releasing a tensile force on the other one of the first and second deflection wires, wherein the means for simultaneously imparting includes a threaded shaft with first threads connected to the adjustment knob for rotation therewith and a slide having second threads that mate with the first threads of the threaded shaft;
wherein the slide is coupled to at least one of the first and second deflection wires, and wherein rotation of the adjustment knob rotates the threaded shaft to linearly displace the slide along a length of the threaded shaft such that the distal end portion of the flexible tubular body deflects from a first configuration to a second configuration; and
wherein the handle outer surface and the knob outer surface are substantially unchanged when the flexible elongate member is disposed in the first and second configurations.

20. The apparatus of claim 19 wherein rotation of the adjustment knob rotates the threaded shaft to cause movement of the first and second deflection members in opposite directions.

* * * * *